US006936471B2

(12) United States Patent
Hajduk et al.

(10) Patent No.: US 6,936,471 B2
(45) Date of Patent: Aug. 30, 2005

(54) INSTRUMENT FOR HIGH THROUGHPUT MEASUREMENT OF MATERIAL PHYSICAL PROPERTIES AND METHOD OF USING SAME

(75) Inventors: Damian Hajduk, San Jose, CA (US); Eric Carlson, Palo Alto, CA (US); J. Christopher Freitag, Santa Clara, CA (US); Oleg Kolosov, Cupertino, CA (US); James R. Engstrom, Ithaca, NY (US); Adam Safir, Berkeley, CA (US); Ravi Srinivasan, Mountain View, CA (US); Leonid Matsiev, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 440 days.

(21) Appl. No.: 09/779,149

(22) Filed: Feb. 8, 2001

(65) Prior Publication Data

US 2002/0029621 A1 Mar. 14, 2002

Related U.S. Application Data

(62) Division of application No. 09/580,024, filed on May 26, 2000.

(51) Int. Cl.[7] .................. G01N 31/00; G01N 3/00; G01N 3/08

(52) U.S. Cl. .............. 436/2; 436/55; 435/DIG. 1; 435/DIG. 2; 435/DIG. 9; 73/760; 73/788; 73/789; 73/826; 73/841; 73/847

(58) Field of Search ............... 435/7.1, DIG. 1, 435/2, DIG. 9; 436/2, 55; 73/760, 788, 789, 826, 841, 847

(56) References Cited

U.S. PATENT DOCUMENTS

| | | |
|---|---|---|
| 1,870,412 A | 8/1932 | Kennedy |
| 3,071,961 A | 1/1963 | Heigl et al. |
| 3,675,475 A | 7/1972 | Weinstein ............ 73/89 |
| 3,713,328 A | 1/1973 | Aritomi |
| 3,798,960 A | 3/1974 | Glass |
| 3,805,598 A | 4/1974 | Corcoran ............ 73/81 |
| 3,818,751 A | 6/1974 | Karper et al. ........ 73/15.6 |
| 3,849,874 A | 11/1974 | Jeffers ............ 29/590 |
| 3,895,513 A | 7/1975 | Richardson |
| 3,908,441 A | 9/1975 | Virgolet |
| 3,933,032 A | 1/1976 | Tschoegl ............ 73/67.1 |
| 4,229,979 A | 10/1980 | Greenwood ............ 73/704 |
| 4,447,125 A | 5/1984 | Lazay et al. ............ 350/96.3 |
| 4,517,830 A | 5/1985 | Gunn et al. |
| 4,567,774 A | 2/1986 | Manahan et al. ............ 73/826 |
| 4,570,478 A | 2/1986 | Soong ............ 73/60 |
| 4,599,219 A | 7/1986 | Cooper et al. |
| 4,602,501 A | 7/1986 | Hirata ............ 73/54 |
| 4,605,589 A | 8/1986 | Orphanides |
| 4,680,958 A | 7/1987 | Ruelle et al. ............ 73/56 |
| 4,685,328 A | 8/1987 | Huebner et al. |
| 4,699,000 A | 10/1987 | Lashmore et al. |
| 4,715,007 A | 12/1987 | Fujita et al. |
| 4,740,078 A | 4/1988 | Daendliker et al. ........ 356/35.5 |
| 4,749,854 A | 6/1988 | Martens ............ 250/225 |
| 4,789,236 A | 12/1988 | Hodor et al. ............ 356/33 |
| 4,793,174 A | 12/1988 | Yau |
| 4,829,837 A | 5/1989 | Telfer |
| 4,893,500 A | 1/1990 | Fink-Jensen ............ 73/60 |
| 4,899,575 A | 2/1990 | Chu et al. |
| 4,899,581 A | 2/1990 | Allen et al. |
| 4,932,270 A | 6/1990 | Lurie et al. ............ 73/862.33 |
| 4,975,320 A | 12/1990 | Goldstein et al. |
| 5,008,081 A | 4/1991 | Blau et al. ............ 422/64 |
| 5,051,239 A | 9/1991 | von der Goltz |
| 5,092,179 A | 3/1992 | Ferguson |
| 5,115,669 A | 5/1992 | Fuller et al. ............ 73/54.39 |
| 5,142,900 A | 9/1992 | Duke ............ 73/54.39 |
| 5,193,383 A | 3/1993 | Burnham et al. ............ 73/105 |
| 5,236,998 A | 8/1993 | Lundeen et al. ............ 525/52 |

(Continued)

FOREIGN PATENT DOCUMENTS

| | | |
|---|---|---|
| EP | 0 317 356 A2 | 5/1989 |
| JP | 02297040 A | 12/1990 |

(Continued)

OTHER PUBLICATIONS

Translation of JP–3–122544 (stapled with Patent).*
Translation of JP–4–366744 (stapled with Patent).*

(Continued)

Primary Examiner—Padmashri Ponnaluri
Assistant Examiner—My-Chau T Tran
(74) Attorney, Agent, or Firm—Dobrusin & Thennisch, PC

(57) ABSTRACT

An apparatus and method for screening combinatorial libraries of materials by measuring the response of individual library members to mechanical perturbations is described. The apparatus generally includes a sample holder for containing the library members, an array of probes for mechanically perturbing individual library members, and an array of sensors for measuring the response of each of the library members to the mechanical perturbations. Library members undergoing screening make up a sample array, and individual library members constitute elements of the sample array that are confined to specific locations on the sample holder. During screening, the apparatus mechanically perturbs individual library members by displacing the sample array (sample holder) and the array of probes. Typically, all of the elements of the sample array are perturbed simultaneously, but the apparatus also can also perturb individual or groups of sample array elements sequentially. The flexible apparatus and method can screen libraries of materials based on many different bulk physical properties, including Young's modulus (flexure, uniaxial extension, biaxial compression, and shear); hardness (indentation), failure (stress and strain at failure, toughness), adhesion (tack, loop tack), and flow (viscosity, melt flow indexing, and rheology), among others.

8 Claims, 15 Drawing Sheets

U.S. PATENT DOCUMENTS

| | | | |
|---|---|---|---|
| 5,269,190 A | 12/1993 | Kramer et al. | |
| 5,271,266 A | 12/1993 | Eschbach | 73/54.33 |
| 5,272,912 A | 12/1993 | Katsuzaki | |
| 5,280,717 A | 1/1994 | Hoseney et al. | 73/54.22 |
| 5,303,030 A | 4/1994 | Abraham et al. | 356/345 |
| 5,305,633 A | 4/1994 | Weissenbacher et al. | 73/82 |
| 5,398,885 A | 3/1995 | Andersson et al. | |
| 5,437,192 A | 8/1995 | Kawamoto et al. | |
| 5,438,863 A | 8/1995 | Johnson | |
| 5,452,614 A | 9/1995 | Kato et al. | |
| 5,452,619 A | 9/1995 | Kawanabe et al. | |
| 5,481,153 A | 1/1996 | Turner | |
| 5,517,860 A | 5/1996 | Lin et al. | |
| 5,520,042 A | 5/1996 | Garritano et al. | |
| 5,532,942 A | 7/1996 | Kitamura et al. | |
| 5,610,325 A | 3/1997 | Rajagopal et al. | 73/54.39 |
| 5,626,779 A | 5/1997 | Okada | 219/201 |
| 5,699,159 A | 12/1997 | Mason | 356/351 |
| 5,700,953 A | 12/1997 | Hlady et al. | 73/105 |
| 5,723,972 A | 3/1998 | Bartol et al. | |
| 5,728,532 A | 3/1998 | Ackley | 435/6 |
| 5,756,883 A | 5/1998 | Forbes | |
| 5,764,068 A | 6/1998 | Katz et al. | 324/727 |
| 5,776,359 A | 7/1998 | Schultz et al. | 252/62.51 |
| 5,817,947 A | 10/1998 | Bergerus | |
| 5,821,407 A | 10/1998 | Sekiguchi et al. | 73/54.28 |
| 5,847,283 A | 12/1998 | Finot et al. | |
| 5,877,428 A | 3/1999 | Scolton | |
| 5,892,157 A | 4/1999 | Syre | |
| 5,922,967 A | 7/1999 | Motoyama | |
| 5,959,297 A | 9/1999 | Weinberg et al. | |
| 5,985,356 A | 11/1999 | Schultz et al. | |
| 5,999,887 A | 12/1999 | Giannakopoulos et al. | |
| 6,004,617 A | 12/1999 | Schultz et al. | |
| 6,010,616 A | 1/2000 | Lewis et al. | |
| 6,013,199 A | 1/2000 | McFarland et al. | |
| 6,030,917 A | 2/2000 | Weinberg et al. | |
| 6,033,913 A | 3/2000 | Morozov et al. | |
| 6,034,240 A | 3/2000 | LaPointe | |
| 6,034,775 A | 3/2000 | McFarland et al. | |
| 6,040,193 A | 3/2000 | Winkler | |
| 6,043,317 A | 3/2000 | Mumick et al. | |
| 6,043,363 A | 3/2000 | LaPointe et al. | |
| 6,045,671 A | 4/2000 | Wu et al. | |
| 6,050,138 A | 4/2000 | Lynch et al. | |
| 6,050,139 A | 4/2000 | Bousfield et al. | |
| 6,087,181 A | 7/2000 | Cong | |
| 6,092,414 A | 7/2000 | Newman | |
| 6,124,476 A | 9/2000 | Guram et al. | |
| 6,149,882 A | 11/2000 | Guan et al. | |
| 6,151,123 A | 11/2000 | Nielson | |
| 6,157,449 A | 12/2000 | Hajduk | |
| 6,175,409 B1 | 1/2001 | Nielsen et al. | |
| 6,177,528 B1 | 1/2001 | LaPointe et al. | |
| 6,182,499 B1 * | 2/2001 | McFarland et al. | 73/24.06 |
| 6,187,164 B1 | 2/2001 | Warren et al. | |
| 6,203,726 B1 | 3/2001 | Danielson et al. | |
| 6,225,487 B1 | 5/2001 | Guram | |
| 6,225,550 B1 | 5/2001 | Hornbostel et al. | |
| 6,242,623 B1 | 6/2001 | Boussie et al. | |
| 6,248,540 B1 | 6/2001 | Weinberg et al. | |
| 6,260,407 B1 | 7/2001 | Petro et al. | |
| 6,265,226 B1 | 7/2001 | Petro et al. | |
| 6,265,601 B1 | 7/2001 | Guram et al. | |
| 6,268,513 B1 | 7/2001 | Guram et al. | |
| 6,294,388 B1 | 9/2001 | Petro | |
| 6,296,771 B1 | 10/2001 | Miroslav | |
| 6,306,658 B1 | 10/2001 | Turner et al. | |
| 6,315,923 B1 | 11/2001 | Devenney et al. | |
| 6,326,090 B1 | 12/2001 | Schultz et al. | |
| 6,336,353 B2 | 1/2002 | Matsiev et al. | |
| 6,393,895 B1 * | 5/2002 | Matsiev et al. | 73/24.06 |
| 6,438,497 B1 * | 8/2002 | Mansky et al. | 702/22 |
| 6,602,714 B1 * | 8/2003 | Tagge et al. | 436/2 |

FOREIGN PATENT DOCUMENTS

| | | | | |
|---|---|---|---|---|
| JP | 3-122544 | * | 5/1991 | G01N/3/00 |
| JP | 3122545 | | 5/1991 | |
| JP | 4-366744 | * | 12/1992 | G01N/3/00 |
| WO | WO 96/11878 | | 4/1996 | |
| WO | WO 98/15501 | | 4/1998 | |
| WO | WO 99/18431 | | 4/1999 | |
| WO | WO 00/17413 | | 3/2000 | |
| WO | WO 00/23921 | | 4/2000 | |
| WO | WO 00/36410 | | 6/2000 | |
| WO | WO 00/40331 | | 7/2000 | |
| WO | WO 00/51720 | | 9/2000 | |
| WO | WO 00/67086 | | 11/2000 | |
| WO | WO 01/79949 A2 | | 10/2001 | |

OTHER PUBLICATIONS

"Micro–Indentation Relaxation Measurements in Polymer Thin Films," D.M. Shinozaki and Y. Lu, *J. Electronic Materials*, vol. 26, No. 7, pp. 852–858, 1997.

"Ultramacroindentation Apparatus for the Mechanical Characterization of Thin Films" P.E. Wierenga and A.J.J. Franken, *J. Appl. Phys.*, 55 (12), pp. 4244–4247, Jun. 15, 1984.

"Microhardness Studies of Polymers and Their Transitions," F.J. Balta Calleja, *TRIP*, vol. 2, No. 12, pp. 419–425, Dec. 1994.

"Evaluation of Young's Modulus of Polymers from Knoop Microindentation Tests," E. Amitay–Sadovsky and H.D. Wagner, *Polymer*, vol. 39, No. 11, pp. 2387–2390, 1998.

"Standard Test Method for Rubber Property—International Hardness," ASTM, D 1415–88, Feb. 1989.

"DMA 2980 Dynamic Mechanical Analyzer," http://www.tainst.com/dma2.html, Dec. 29, 2000.

"Introducing the New DMTA V!," http://www.rheometricscientific.com/dmtaV.htm, Dec. 29, 2000.

Robert H. Lacombe and Jeremy Greenblatt, "Mechanical Properties of Thin Polyimide Films," Proc. Tech. Conf. Polyimides (First) 1982, published in *Polyimides: Synth., Charact., Appl.*, pp. 647–668, 1984.

U.S. Appl. No. 09/939,404 entitled "High Throughput Mechanical Property and Bulge Testing of Material Libraries," (D. Hajduk et al.) filed Aug. 24, 2001.

U.S. Appl. No. 09/939,252 entitled "High Throughput Mechanical Rapid Serial Property Testing of Material Libraries," (P. Mansky) filed Aug. 24, 2001.

U.S. Appl. No. 09/939,139 entitled "High Throughput Fabric Handle Screening," (M. Kossuth et al.) filed Aug. 24, 2001.

U.S. Appl. No. 09/939,149 entitled "High Throughput Rheological Testing Of Materials" (Paul Manksy et al.) filed Aug. 24, 2001.

U.S. Appl. No. 09/939,263 entitled "High Throughput Mechanical Property Testing of Materials Libraries Using Capacitance," (D. Hajduk et al.) filed Aug. 24, 2001.

U.S. Appl. No. 09/938,994 entitled "High Throughput Mechanical Property Testing of Materials Libraries Using a Piezoelectric," (D. Hajduk) filed Aug. 24, 2001.

The family of applications for U.S. Appl. No. 09/174,856 titled "Graphic Design of Combinatorial Material Libraries" (Lacy, et al.) filed Oct. 19, 1998.

U.S. Appl. No. 09/578,997 entitled "High Throughput Viscometer and Method of Using Same" filed May 25, 2000.

Odian, Principles of Polymerization, 3rd Ed., John Wiley & Sons, Inc. (1991).

Timoshenko, S., Theory of Plates and Shells, McGraw–Hill, New York 1940.

European Search Report dated Dec. 10, 2001.

U.S. Appl. No. 09/420,334 entitled "Graphic Design of Combinatorial Material Libraries" (Lacy, et al.) filed Oct. 18, 1999.

U.S. Appl. No. 09/305,830 titled "Synthesizing Combinatorial Libraries of Materials" (Rust, et al.) filed May 5, 1999.

U.S. Appl. No. 09/550,549 entitled "Automated Process Control And Data Mangement System And Methods" (Crevier, et al.) filed Apr. 14, 2000.

U.S. Appl. No. 09/755,623 entitled "Laboratory Database System and Methods For Combinatorial Materials Research" (Dorsett, Jr., et al.) filed Jan. 5, 2001.

The family of applications for U.S. Appl. No. 09/227,558 entitled, "Apparatus and Method of Research for Creating and Testing Novel Catalysts, Reactions and Polymers" (Turner et al.) filed Jan. 8, 1999.

U.S. Appl. No. 09/235,368 entitled "Polymerization Method From the Combinatorial Synthesis and Analysis of Organometallic Compounds and Catalysts" (Weinberg et al.) filed Jan. 21, 1999.

Provisional U.S. Appl. No. 60/122,704 entitled "Controlled, Stable Free Radical Emulsion and Water–Based Polymerizations" (Klaerner et al.) filed Mar. 9, 1999.

The family of applications for U.S. Appl. No. 09/156,827 entitled "Formation of Combinatorial Arrays of Materials Using Solution–Based Methodologies" (Giaquinta et al.) filed Sep. 18, 1998.

The family of applications for U.S. Appl. No. 09/567,598 entitled "Polymer Libraries on a Substrate, Method for Forming Polymer Libraries on a Substrate and Characterization Methods with Same" (Boussie et al.) filed May 10, 2000.

U.S. Appl. No. 09/579,338 entitled "Rheo–Optical Indexer and Method of Screening and Characterizing Arrays of Materials" (Carlson et al.) filed May 25, 2000.

Bowlt, C., "A Simple Capillary Viscometer" Physics Education, Mar. 1975, vol. 10, No. 2, pp. 102–103.

Young, W.C., Roark's Formulas for Stress and Stain, 1989.

Ali, S.I. and Shahida Begum, "Fabric Softeners and Softness Perception", Ergonomics, v.37, No. 5, pp. 801–806 (1994).

Osterberg, Peter M. and Stephen D. Senturia, "M–TEST: A Test Chip for MEMS Material Property Measurement Using Electrostatically Actuated Test Structures," Journal of Microelectromechanical Systmes, vol. 6, No. 2, Jun. 1997.

Kim J.O. and B. Lewis Slaten, "Objective Assessment of Fabric Handle in Fabrics Treated With Flame Retardants," Journal of Testing and Evaluation, JTEVA, vol. 24, No. 4, Jul. 1996, pp. 223–228.

Raeel, Mastura and Jiang Liu, "An Empirical Model for Fabric Hand" Textile Research Journal 62, 1, pp. 31–38 (1991).

Pan, Ning and K.C. Yen, "Physical Interpretations of Curves Obtained Through the Fabric Extraction Process for Handle Measurement," Textile Research Journal 62(5), pp. 279–290 (1992).

"Handle–O–Meter", Thwing–Albert Instrument Company, Philadelphia, PA.

Grover, G. et al., "A Screening Technique for Fabric Handle", J. Text. Inst., 1993, 84 No. J. Textile Institute, pp. 486–494.

* cited by examiner

INSTRUMENT FOR HIGH THROUGHPUT MEASUREMENT OF MATERIAL PHYSICAL PROPERTIES AND METHOD OF USING SAME

This application is a divisional of copending U.S. patent application Ser. No. 09/580,024, filed May 26, 2000, which is herein incorporated by reference for all purposes.

BACKGROUND

1. Technical Field

The present invention relates to an apparatus and method for determining physical characteristics of an array of materials as functions of mechanical perturbations and environmental conditions.

2. Discussion

Combinatorial chemistry generally refers to methods and materials for creating collections of diverse materials or compounds—commonly known as libraries—and to techniques and instruments for evaluating or screening libraries for desirable properties. Combinatorial chemistry has revolutionized the process of drug discovery, and has enabled researchers to rapidly discover and optimize many other useful materials.

Scientists realized that efficient screening techniques were essential for any successful combinatorial research effort. However, since much of the original work in combinatorial chemistry focused on biologically active compounds, early researchers typically employed conventional biological assays as screening methods. Many of these assays were ideally suited for screening combinatorial libraries because they required little or no sample preparation and they could generate useful results using small sample sizes (a mg or less) generally produced in a combinatorial synthesis.

But as researchers began applying combinatorial methods to develop novel non-biological materials, they increasingly found that conventional instruments and methods for characterizing materials were often unsatisfactory for screening. For example, instruments for characterizing physical properties of materials—viscometers, rheometers, dynamic analyzers, and other mechanical property test instruments—are generally unsuitable for screening purposes because they were designed to process one sample at a time. Although the throughput of these serial instruments would likely benefit from automation, many mechanical property test instruments require time-consuming sample preparation, demand more sample than is ordinarily prepared in a high speed research program, and exhibit sluggish environmental control, making such instruments impractical for use as screening tools. Furthermore, the long time scales associated with measuring mechanical properties of polymers, ceramics and other engineered materials often make serial approaches unsuitable as screening methods.

Moreover, competitive pressures are forcing scientists to continually expand their set of screening tools. Many material scientists have embraced combinatorial methodologies because the techniques allow them to develop novel materials in a fraction of the time as conventional discovery methods. This has allowed researchers to tackle a wider range of material design challenges and to consider a broader set of characteristics that ultimately translates into improved material performance. Of course, new design challenges and additional screening criteria mean that laboratories must acquire more screening tools, which if purchased as separate instruments, might offset cost savings associated with combinatorial methods.

Thus, there exists a need for versatile instruments and techniques for screening combinatorial libraries, and especially instruments and methods for measuring physical properties of materials. The present invention, at least in part, satisfies that need.

SUMMARY OF THE INVENTION

The present invention provides an apparatus and method for screening combinatorial libraries that addresses many of the problems encountered when using conventional instruments. For example, the disclosed apparatus can measure physical properties of library members in parallel and can perform tests on small amounts of material, which are easily prepared by automated liquid and/or solid handling techniques. Compared to conventional instruments, the disclosed apparatus affords faster sample loading and unloading, for example, through the use of disposable sample arrays and test probes. The present invention is operationally flexible, and permits a single instrument to perform many different material tests through proper selection of sample array format and test probe design. Rapid serial measurements may also be performed.

Thus, one aspect of the present invention provides and apparatus for measuring bulk physical properties of an array of material samples. The apparatus includes a moveable sample holder for containing the array of material samples, and an array of probes for mechanically perturbing the array of material samples. The apparatus also includes an actuator for translating the moveable sample holder and the array of material samples. The actuator moves the array of material samples in a direction normal to a plane defined by the ends of the probes so that the material samples contact the probes. In addition, the apparatus includes a sensor for monitoring the response of the materials to mechanical perturbation by the probes. Typical sensors include force sensors.

A second aspect of the present invention provides a system for screening a combinatorial library of materials by measuring bulk physical properties of the materials. The system includes an array of material samples and probes for mechanically perturbing the samples. Depending on the particular physical property being tested, the array includes materials deposited at predefined regions on flexible or rigid substrates, or materials contained in a group of vessels. The system also includes an actuator for translating the array of material samples in a direction normal to a plane defined by the ends of the probes so the material samples contact the probes. The system also includes a sensor for monitoring the response of the array of material samples to mechanical perturbations by the probes.

A third aspect of the invention provides a method of screening a combinatorial library of materials. The method includes providing an array of material comprising at least five individual samples, and mechanically perturbing the array of materials by contacting at least two of the material samples with probes simultaneously. In addition, the method includes monitoring responses of the samples during the mechanical perturbations. Depending on type of mechanical perturbation, the method can screen libraries of materials based on measurements of many different bulk physical properties. For example, the inventive method can measure physical properties related to Young's modulus—including flexure, uniaxial extension, biaxial compression, and shear. In addition, the method can measure physical properties related to hardness (indentation), failure (stress and strain at failure, toughness), adhesion (tack, loop tack), and flow (viscosity, melt flow indexing, and rheology), among others.

DETAILED DESCRIPTION OF THE PREFERRED EMBODIMENTS

Overview of Apparatus and Method

Figure 1:
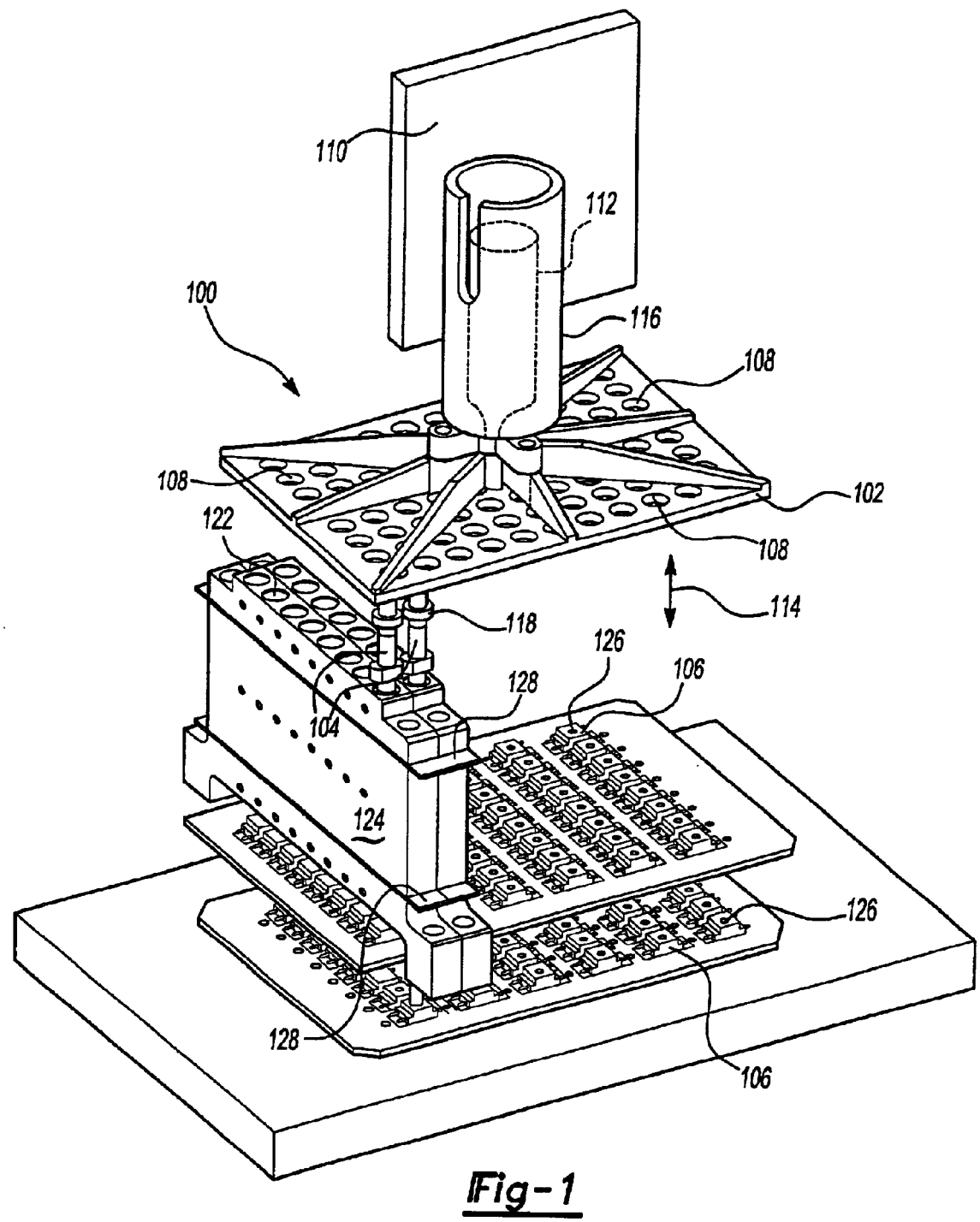
FIG. 1 is a perspective view of one embodiment of a parallel dynamic mechanical analyzer (PDMA).

The present invention comprises a system and method for screening combinatorial libraries of materials by measuring the response of individual library members to mechanical perturbations. Throughout and in accord with this specification, the number of member of a combinatorial library of materials may vary depending on the embodiment being practiced. Generally, an array of materials comprises a plurality of materials for which a property measurement is desired. In some embodiments, an array of materials will comprise 8 or more, 16 or more, 24 or more or 48 or more materials, each of which is different from the others. Arrays of materials and methods of making such arrays are described in detail, for example, U.S. Pat. Nos. 6,004,617 and 6,030,917 and U.S. patent application Ser. No. 09/227,558, filed Jan. 8, 1999, all of which are incorporated herein by reference for all purposes. The materials in the arrays may be any type of material for which a property measurement is desirable. Examples of the types of materials that may be in an array include non-biological polymers (such as polyethylene, polypropylene, polystyrene, polymethacrylic acid, polyacrylamide, polymethylmethacrylate and the like, including copolymers or higher order polymers of the same monomers), metals (including all types of alloys), composites, etc. The materials in the array may be in various forms, including amorphous, crystalline and mixtures thereof. The only limitation on the type of material is that the material must be capable of being deposited in a manner compatible with the property testing described herein. Those of skill in the art will appreciate from this specification that members of the array may be the same or different materials. Also, standards (such as calibration standards) or blanks may be employed in the array for known scientific purposes. Relative comparison of the properties of members of the array is a particularly useful embodiment of this invention.

Throughout this specification, the specific embodiment discussed in detail is a ninety-six parallel embodiment. This particularly preferred embodiment has many detailed features, which may not be necessary in other embodiments of this invention. For example, force sensors are placed remotely to the samples and are set at certain spacing. Those of skill in the art can easily modify such design parameters for other embodiments, such as by placing the sensors at other spacing, not placing the sensors substantially in a plane and not placing the samples remote to the sensors (e.g., using an integrated probe and sensor). These are design choices for the present invention and describe other embodiments of the invention.

Those of skill in the art will also appreciate that lower or higher throughput may serve the needs of a particular application of this invention. Thus, 8 or more, 16 or more, 24 or more or 48 or more test probes in parallel are within the scope of this invention. These probes may all be in the same test fixture or in multiple test fixtures. Also, different types of probes described herein may be in a single test fixture. In terms of throughput, a single material (e.g., a sample) may have up to ten different properties measured simultaneously. In addition, up to 96 materials may have one or more properties measured simultaneously in 10 minutes or less, preferably 5 minutes or less and even more preferably in 1 minute or less. In some embodiments, throughput of 30 seconds or less or even 10 seconds or less may be accomplished for an array of the sizes discussed herein, e.g., up to 96 materials in the array.

Generally, the samples are associated with specific locations or regions of the sample holder such that the location of individual samples may be known. Thus, samples may be contained by the sample holder, placed on the specific locations of the sample holder or fixed to the sample holder (e.g., if the sample holder is replaceable) or otherwise specifically located. The method of knowing the location of an individual sample is not critical to this invention and is described herein based on the samples being contained in the sample holder for illustration purposes only. Also generally, preferred embodiments of attachment means are described for various parts (such as clamping, threading, magnetic coupling, springs, etc.), but those of skill in the art will appreciate that this is simply a matter of design choice and the invention herein is not limited to the specific embodiments described in detail.

As used in this disclosure, the term "mechanical perturbations" generally refers to controlled straining and/or shearing of a library member. The actual displacement of the material may be small (for example, about thirty $\mu m$ or less). The system generally includes a sample holder for containing or securing the library members, one or more probes for mechanically perturbing individual library members, and one or more sensors for measuring the response of each of the library members to the mechanical perturbations. Library members undergoing screening make up a sample array, and individual library members constitute elements of the sample array that are confined to specific locations on the sample holder. Although the system can screen libraries of varying size, a most preferred embodiment is a library comprising an eight-by-twelve rectangular array of material samples in which, similar to a standard ninety-six well microtiter plate, the centers of adjacent array elements are spaced nine-mm apart.

During screening, the probes mechanically interact with the elements of the sample array. In some embodiments the probes have about the same lateral spacing as the elements of the sample array so that there is a one-to-one correspondence between individual probes and sample array elements. In addition, since the sample array and the ends of the probes also define two generally planar surfaces, the system can perturb all of the sample array elements simultaneously by displacing the sample array (sample holder) and/or the probes in a direction normal to the two surfaces. If adapted to perturb all of the elements simultaneously, the system may include a rectilinear translation stage that is attached to the sample holder or the probes. In other embodiments, the system may perturb individual or groups of sample array elements. In these embodiments, the system may include a translation mechanism capable of three-dimensional motion, which is attached to a single probe, to a group of probes, or to the sample holder.

Since the bulk physical properties of materials can depend strongly on environmental conditions—temperature, pressure, ambient gas composition (including humidity), electric and magnetic field strength, and so on—the screening system may include a control system for regulating environmental conditions. Useful control systems include an environmental chamber that encloses the sample holder, the sample array, and the probes. As discussed below, the system may locate the sensors outside of the environmental chamber if their performance is strongly influenced by any of the environmental control variables, such as temperature.

The system uses software running on a general-purpose computer to control the mechanical perturbations and to acquire and record the response of the sample array elements to the mechanical perturbations. Computer software also regulates conditions in the environmental chamber, if present. As discussed below, one or more data acquisition boards, which are under the direction of the software, link the computer to the peripheral control elements, sensors, and so on.

The versatile system can screen libraries of materials based on many different bulk physical properties. For example, the system can measure physical properties related to Young's modulus—including flexure, uniaxial extension, biaxial compression, and shear. In addition, the system can measure physical properties related to hardness (indentation), failure (stress and strain at failure, toughness), adhesion (tack, loop tack), and flow (viscosity, melt flow indexing, and rheology), among others. As described below, the system can choose from among many screening criteria or physical properties by selecting the proper sample array format and probe design.

Parallel Dynamic Mechanical Analyzer (PDMA)

FIG. 1 shows a prospective view of a parallel dynamic mechanical analyzer (PDMA) 100 that can be used to screen a library of materials by measuring responses of the materials to mechanical perturbations. The PDMA 100 includes a sample holder 102 for containing or securing the library members, probes 104 for perturbing individual library members, and sensors 106 (e.g., force sensors) for measuring the response of each of the library members to the mechanical perturbations. The library members comprise a sample array (not shown) in which individual library members constitute elements of the sample array that are confined to specific locations 108 on the sample holder 102. The particular sample holder 102 shown in FIG. 1 contains a sample array comprised of an eight-by-twelve rectangular array of material samples located on nine-mm centers. But in general, the PDMA can analyze sample arrays having two or more elements, and preferably, at least eight elements to ensure adequate screening throughput. The PDMA 100 generally has as many probes 104 as desired, for example there may be as many as there are samples in the array, although for clarity, FIG. 1 shows only two probes 104. In the embodiment shown in FIG. 1, each of the probes 104 has about the same lateral spacing as the elements of the sample array so that one probe 104 is associated with one sample array element. Alternatively, the PDMA may employ fewer probes 104 than sample array elements, so that a probe or group of probes perturbs multiple sample array elements. Alternatively, there may be more probes than samples.

The PDMA 100 includes first 110 and second 112 translation actuators for displacing the sample array in a direction normal 114 to surfaces containing the sample array and the ends of the probes 104. The first translation actuator 110, which is attached to the sample holder 102 via a housing 116 that surrounds the second translation actuator 112, provides relatively coarse displacement of the sample holder 102. A useful first translation actuator 110 includes a motorized translation stage available from POLYTEC PI under the trade name M-126 Translation Stage, which has a translation range of twenty-five mm and a resolution of 0.1 $\mu m$. The second translation actuator 112, which is attached directly to the sample holder 102, provides relatively fine displacement of the sample holder 102. A useful second translation actuator 112 includes a preloaded piezoelectric stack available from Polytec PI under the trade name P-753 LISA Linear PZT Stage Actuator, which has a translation range of 30 $\mu$m and can provide an 100-N pushing force and a 20-N pulling force. Other embodiments for these parts will be within the scope of those of skill in the art. The PDMA 100 typically controls the first 110 and second 112 translation actuators using a DC motor controller and an amplifier/position servo controller, respectively, which are linked to a general-purpose computer (not shown). In an alternative embodiment, the first 110 translation actuator is mounted on an x-y translation stage (not shown), which allows movement of the sample holder 102 in a direction about parallel to the surfaces containing the sample array and the ends of the probes 104. This latter embodiment is useful when the sample holder 102 must be moved laterally to align different groups of sample array elements with the probes 104 during screening—i.e., when the PDMA employs fewer probes 104 than sample array elements and the probes 104 are stationary.

Each of the probes 104 includes a test fixture 118 that contacts one of the sensors 106 through a solid or composite shaft 120 shown in phantom in FIG. 1. Each shaft 120 passes through an aperture 122 in an isolation block module 124 that separates the probe test fixture 118 from the sensor 106. For clarity, FIG. 1 shows only two isolation block modules 124, although this embodiment of the PDMA 100 ordinarily includes twelve such modules 124—one isolation block module 124 for each row of eight probes 104. Alternatively, the PDMA may include a single isolation block for separating the probe test fixtures 118 from the sensors 106. For reliable measurements, each test fixture 118 should contact its associated sample array element in a specific location 108 on the sample holder 102. This requires a mechanism for locating the composite shaft 120 along a line extending from the center 126 of a particular sensor 106, normal to the surface of the sample array. Although conventional linear bearings can be used to align the composite shaft 120, friction between the linear bearings and the shaft 120 limits the displacement resolution at low force levels. In addition, the PDMA can also use air bearings, but the size and expense of air bearings often make them impractical for use with a PDMA employing relatively large numbers of probes 104.

Figure 2:
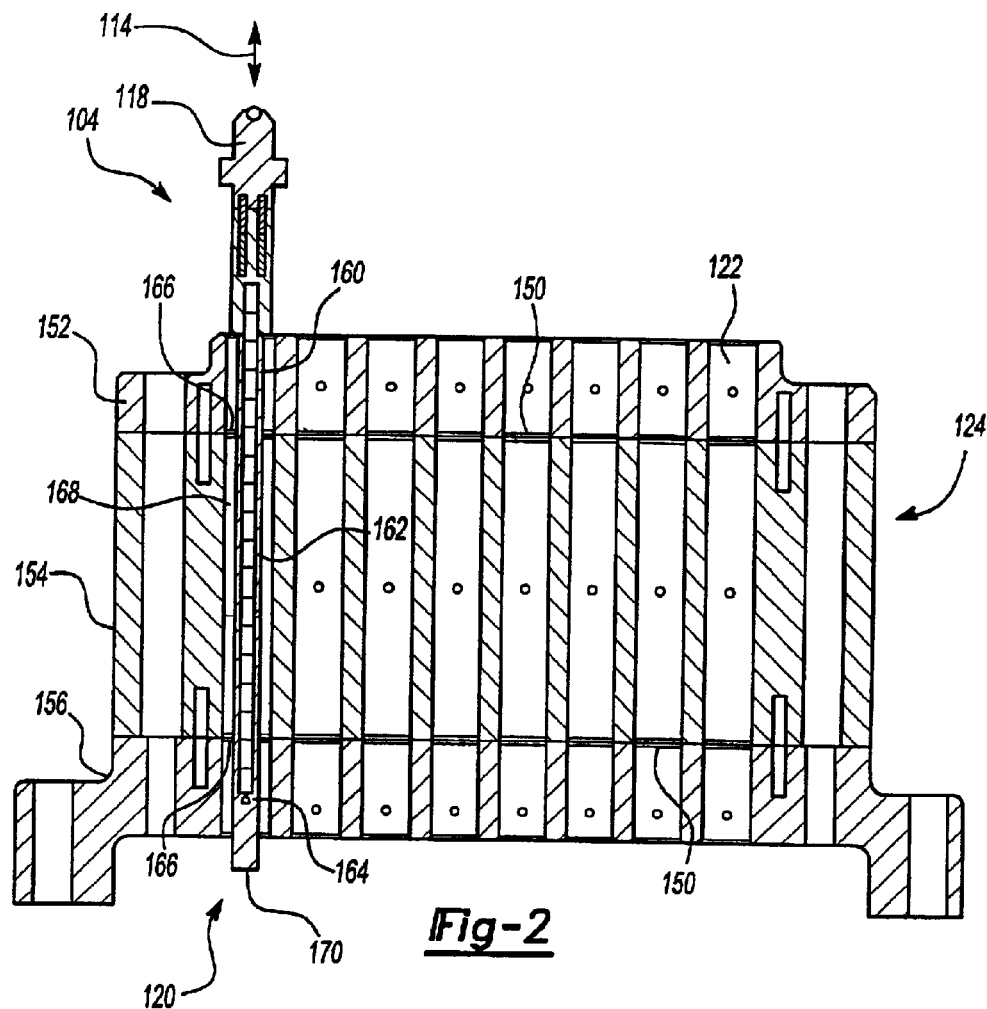
FIG. 2 shows a cross-sectional view of an isolation block module that separates the probe test fixtures and the sample array from the force sensors.

FIG. 2, which illustrates the use of two flexure strips 150 to align the probes 104 with the sample array elements, shows a cross-sectional view of one of the isolation block modules 124 as seen through a cutting plane containing centerlines of the apertures 122 shown in FIG. 1. The flexure strips 150 are sandwiched between generally planar surfaces of upper 152 and intermediate 154 segments of the isolation block module 124 and between generally planar surfaces of the intermediate 154 and lower 156 segments of the isolation module 124. The two flexure strips 150 shown in FIG. 2 comprise relatively thin (from about $10^1$ $\mu$m to about $10^2$ $\mu$m) rectangular membranes having spaced-apart holes that are substantially aligned with each composite shaft 120 within the apertures 122 of the isolation block modules 124.

As shown in FIG. 2, the composite shaft 120 is comprised of a rigid, substantially cylindrical core 158 and a thermally insulating outer sheathing having upper 160, intermediate 162, and lower 164 sections that are threaded onto the core 158. When installed in the apertures 122, the abutting ends of the upper 160 and intermediate 162 sections of the sheathing and the intermediate 162 and lower 164 sections of the sheathing lie in planes containing the two flexure strips 150. Since the diameters of the core 158 and the holes in the flexure strips 150 are about the same, the periphery of the holes are clamped between the abutting ends of the upper 160, intermediate 162, and lower sections of the sheathing. The flexure strips 150 are also clamped along the periphery of each aperture 122, adjacent interfaces between the upper 152, intermediate 154, and lower segments 156 of the isolation block module 124. The resulting clamped membranes or diaphragms 166, which span annular gaps 168 between the shafts 120 and the isolating block module 124, support and align the probes 104.

The geometry of the diaphragms 166 makes each of the flexure strips 150 compliant for displacements normal 114 to the surface supporting or containing the sample array, but mechanically stiff for displacements parallel to the sample array. The use of two flexure strips 150 also makes each combination of shaft 120 and diaphragms 166 mechanically stiff for angular displacements away from the direction normal 114 to the surface of the sample array. Moreover, through proper selection of materials and dimensions, the flexure strips 150 exhibit effective spring constants—for displacements normal 114 to the sample array—substantially less than effective constants of the sensors 106. In this way, the flexure strips 150 ordinarily exert minimal influence on the measured responses to mechanical perturbations, unless they are used to "pre-load" the sensors 106 as discussed below. Useful materials for the flexure strips 150 include metallic and polymeric films. For example, one particularly useful flexure strip material is polyimide film, which is available from DuPont under the trade name KAPTON in thickness ranging from about from about thirteen $\mu$m to about one hundred twenty five $\mu$m. Other useful flexure materials include stainless steel foil, diaphrams (in general) and corrugated bronze, for example, the flexure may be mechanically machined stainless steel. Since the effective spring constants of the diaphragms 166 and typical sensors 106 are temperature-dependent, the use of thermally insulating sheathing 160, 162, 164 on the shafts 120 permits the PDMA 100 to vary the temperature of the sample arrays without significantly affecting the measured response.

As noted previously, an important feature of the PDMA 100 is its ability to screen materials based on many different physical properties. One way the PDMA 100 achieves this flexibility is by using interchangeable (and, in some embodiments, disposable) test fixtures 118 with an appropriate sample array format and sample holder 102. For example, one screening method may employ a probe 104 equipped with a ball-tip indenter test fixture 118 to rank the hardness of material samples arrayed on a rigid plate. Another screening method may employ a probe 104 fitted with a flat-tip stylus test fixture 118 to deduce Young's modulus from flexure measurements of material samples arrayed on a flexible substrate. In either case, the PDMA 100 should provide a mechanism for removing and securely attaching the test fixtures 118. Suitable attachment mechanisms include mechanical and electromagnetic couplings, as well as devices employing permanent magnets.

Figure 3:
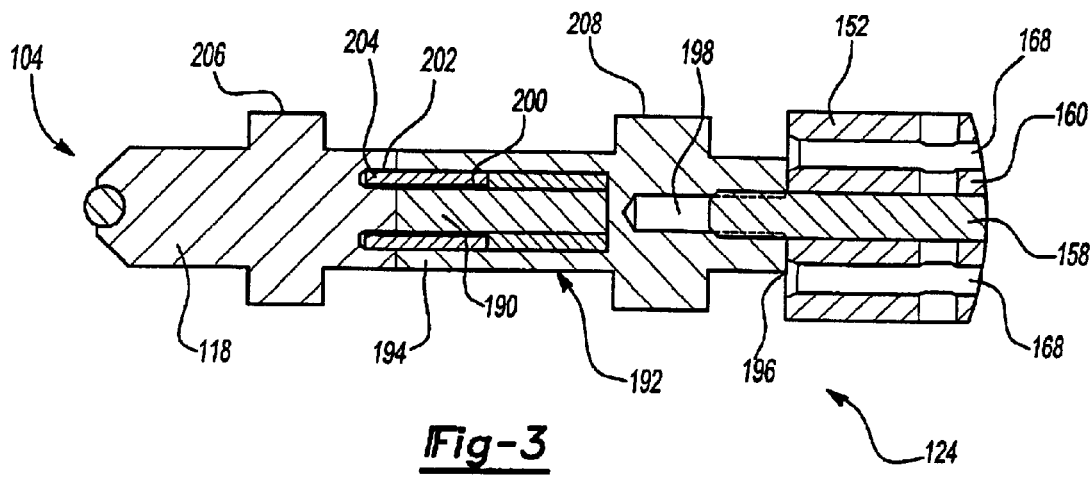
FIG. 3 shows a close-up cross sectional view of the probe shown in FIG. 2, and illustrates the use of a permanent magnet to attach the test fixture to the threaded cylindrical core of the composite shaft.

FIG. 3 shows a close-up cross sectional view of the probe 104 shown in FIG. 2, and illustrates the use of a permanent magnet 190 to attach the test fixture 118 to the threaded core 158 of the composite shaft 120. As shown in FIG. 3, the probe 104 includes a base 192 having first 194 and second ends 196 that adjoin, respectively, the test fixture 118 and the upper section 160 of the thermally insulating outer sheathing. A substantially cylindrical bore 198 extends partway into the base 192 and is sized and threaded to connect the core 158 of the shaft 120 to the second end 196 of the base 192. The test fixture 118 is removably attached to the first end 194 of the base 192 by magnetic flux originating from the permanent magnet 190 that is embedded in the base 192 of the probe 104. A tubular magnetic shield 200, which typically has a lower modulus than either the probe base 192 or the permanent magnet 190, is wedged into an annular space between the probe base 192 and the permanent magnet 190. The shield 200, which helps secure the magnet 190 within the probe base 192, extends outward from the first end 194 of the base 192 and mates with a substantially circular slot 202 formed in the test fixture 104. The slot 202 is sized to receive the tubular shield 200 with minimal interference, and the shield 200 has a tapered end 204 that helps guide it into the slot 202 during attachment of the test fixture 118 to the probe base 192. In the embodiment shown in FIG. 3, the test fixture 118 and the probe base 192 include flanges 206, 208 for accessing them during removal or attachment.

As can be seen in FIG. 3, the test fixture 118, the base 192, and the shield 200 enclose the permanent magnet 190, which helps minimize stray magnetic flux that may influence sample measurements of nearby probes 104. Generally, the probe 104 components are made from materials having a high magnetic permeability—a relative permeability substantially greater than unity—to ensure effective magnetic shielding. Suitable materials include nickel-iron alloys containing copper, molybdenum, or chromium and mixtures thereof. A particularly useful shielding material is available under the trade name HI-PERM 49 from Carpenter Technology. Other useful shielding materials include cold-rolled steel that has been chrome-plated to resist corrosion. The permanent magnet 190 should be fabricated from a material that provides sufficient force to secure the test fixture 118 to the probe base 192 during screening. Useful permanent magnets 190 include samarium cobalt magnets, ceramic ferrite magnets, aluminum-nickel-cobalt magnets, and neodymium-iron-boron magnets.

Figure 4:
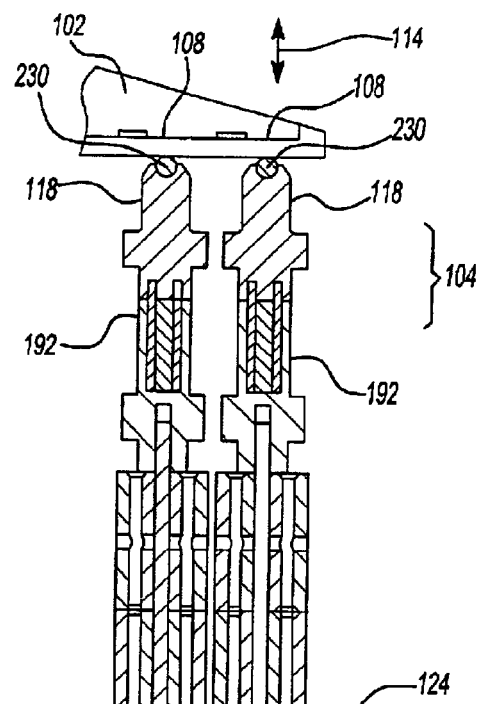
FIG. 4 shows a cross sectional view of two adjacent isolation block modules, and illustrates interactions of probes and force sensors.
Figure 4:
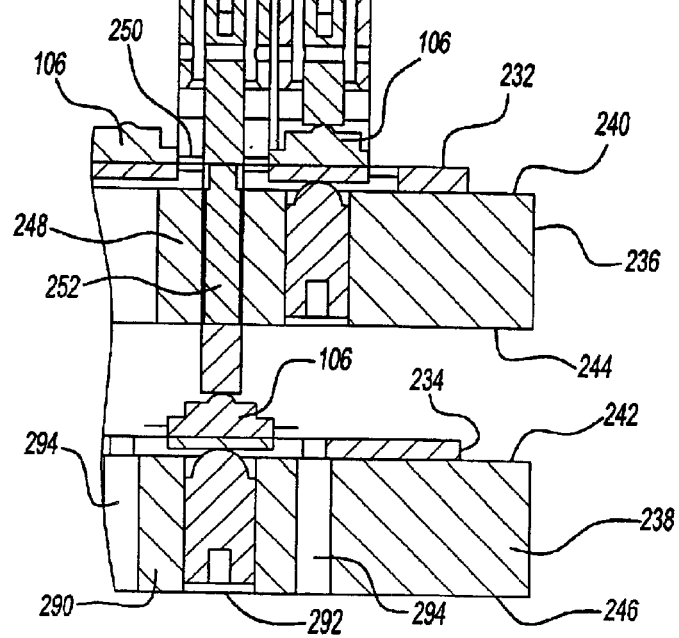

FIG. 4 illustrates interactions of the probes 104, the sensors 106, and a material sample array 230. FIG. 4 shows a cross sectional view of the PDMA 100 of FIG. 1 taken from a plane that cuts through the two isolation block modules 124 and contains centerlines of two adjacent probes 104. During screening, each test fixture 118 portion of the probes 104 interacts with one element of the sample 230 array, which is positioned at a predefined location 108 of the sample holder 102. Movement of the sample holder 102 in a direction normal 114 to the surface of the sample array 230 results in forces that are transmitted to the sensors 106 via each probe test fixture 118, probe base 192, and composite shaft 120. Each composite shaft 120, which includes a rigid core 158 and thermally insulating outer sheathing 160, 162, 164, contacts the force sensor 106 directly or indirectly as discussed below.

The relatively large footprint of each sensor 106 shown in FIG. 4 makes it impracticable to mount all of the sensors 106 on a single plane while maintaining nine-mm spacing between centers 126 of adjacent sensors 106. Of course, using sensors with smaller footprints may allow for mounting in a single plane. To provide nine-mm spacing, the PDMA 100 employs sensors 106 mounted on first 232 and second 234 sensor boards, which rest on upper 236 and lower 238 rigid support plates, respectively. Both support plates 236, 238 include holes that extend from top surfaces 240, 242 of the plates 236, 238 to bottom surfaces 244, 246 of the plates 236, 238. The holes are arrayed on nine-mm centers, and are either threaded or non-threaded. Non-threaded holes 248 in the upper support plate 236 are substantially aligned with through-holes 250 in the first sensor board 232. The non-threaded holes 248 and the through-holes 250 are sized to provide passageways for rods 252 that transmit forces from the composite shafts 120 to sensors 106 mounted on the second (lower) sensor board 234. The PDMA 100 thus maintains the most preferred spacing by distributing the force sensors 106 among two boards 232, 234—thereby doubling the surface area available to mount the force sensors 106—and by arranging the sensors 106 so their centers 126 are nine-mm apart when projected on the surface of the sample array 230. When using smaller sensors or when nine-mm spacing is not desired, the PDMA may dispense with one of the two sensor boards. As many sensor boards as is practical for a particular embodiment may be employed.

Figure 5:
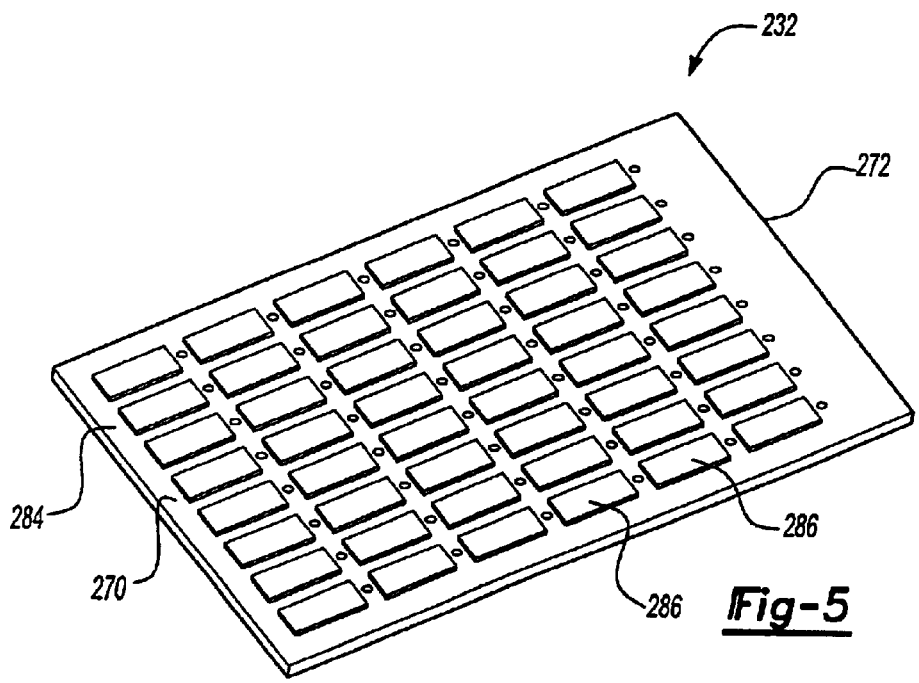
FIG. 5 shows a perspective bottom view of one of the sensor boards.
Figure 6:
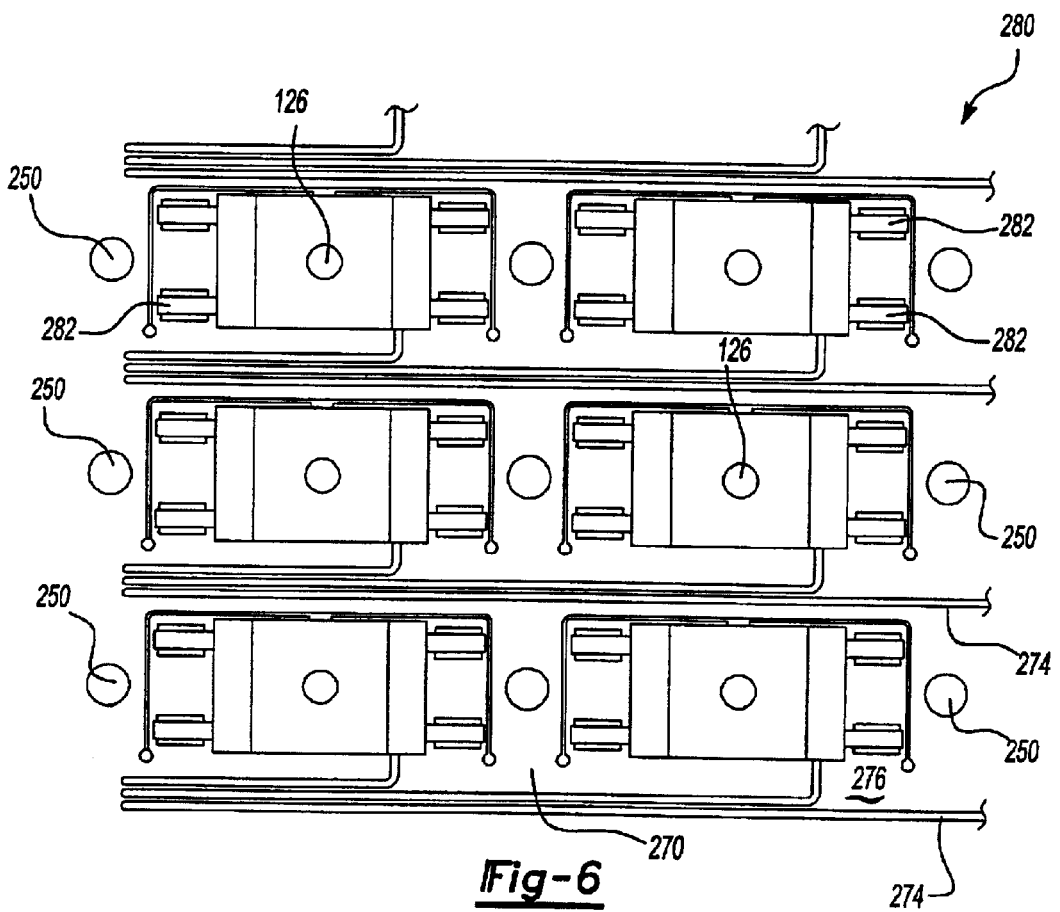
FIG. 6 shows a top view of a portion of one of the sensor boards.

FIG. 5 and FIG. 6 provide further details of the sensors 106 and sensor boards 232, 234, showing respectively, a bottom perspective view and a close-up top view of the first sensor board 232. The first 232 and second 234 sensor boards generally comprise a flexible multi-layer dielectric sheet 270 (e.g., polyimide) and a rigid frame 272 (e.g., FR-4 epoxy glass laminate) that is bonded to the periphery of the dielectric sheet 272. Electrically conductive traces 274 are embedded on top 276 or bottom surfaces 278 of the dielectric sheet 270, or between layers of the flexible sheet 270, forming a double-sided flex circuit 280. Each sensor 106 is mounted on the top surface 276 of the flex circuit 280, and leads 282 on the sensors 106 are connected to conductive traces 274 that terminate at a standard card edge connector 284. Conventional ribbon cables can be used to link the card-edge connector 284 with peripheral recording and control devices (not shown) allowing communication between the sensors 106 and the peripheral devices.

As shown in FIG. 5, the first 232 and second 234 sensor boards include generally planar stiffeners 286 (e.g., FR-4 epoxy glass laminates) attached to the bottom surface 278 of the sensor boards 232, 234 directly below the sensors 106. Each of the stiffeners 286 has about the same footprint as the sensors 106, and helps distribute loads on, and prevent bending of, the sensors 106. Note however, the stiffeners 286 do not prevent movement of the sensors 106 in a direction normal 114 to the sample array 230 since the sensors 106 are mounted on the flexible dielectric sheet 270. Although other embodiments can use rigidly-mounted sensors, the PDMA 100 shown in FIG. 1 uses sensors 106 mounted on the flex circuit 280 to allow "pre-loading" of the sensors 106 as discussed below. Pre-loading may of course be performed by other methods, which those of skill in the art will appreciate from a review of this specification.

The first sensor board 232 shown in FIG. 6 also includes a plurality of through-holes 250 that are located between the sensors 106. Following assembly of the PDMA 100, the through-holes 250 are substantially aligned with unthreaded holes 248 in the upper support plate 236 (FIG. 4). As noted above, the unthreaded holes 248 in the upper support plate 236 provide passageways for rods 252 that transmit forces from the composite shafts 120 to sensors 106 mounted on the second (lower) sensor board 234. Thus, the centers 126 of the sensors 106 and the through-holes 250 of the first sensor board 232 are arrayed on nine-mm centers.

Referring to FIG. 4–6, threaded holes 288, 290 in the upper 236 and lower 238 support plates are sized to receive set-screws 292 that the PDMA 100 can use to pre-load each of the sensors 106 mounted on either the first 232 or second 234 sensor boards. As noted in the description of FIG. 2, the flexure strips 150 used to align the probes 104, are compliant for displacements normal 114 to the plane containing the sample array 230, but are mechanically stiff for displacements in other directions. Moreover, the effective spring constants of the flexure strips 150 are substantially less than the spring constants of the sensors 106 so that the flexure strips 150 ordinarily exert minimal influence on the measured responses of the sample array 230 to mechanical perturbations. However, since the sensors 106 are mounted on the flex circuit 280, the set-screws 292 can apply a force to the stiffeners 286 and the sensors 106 in absence of a force on the test fixture 118. A force recorded by the sensors 106 will therefore be the sum of the force acting on the test fixture 118 and the pre-load force. Since many commercial force sensors can detect only tensile or compressive loads, pre-loading permits a compressive sensor to detect small tensile loads, or a tensile sensor to record small compressive loads, expanding the capabilities of the PDMA 100. Note that the lower support plate 238 and the second sensor board 234 both include unthreaded holes 294, 296 that provide access to the set-screws 292 in the upper support plate 236.

The PDMA 100 can use a wide variety of sensors 106, including miniature force sensors. Most of the sensors 106 incorporate signal conditioning electronics. Suitable force sensors include piezoresistive micromachined silicon strain gauges that form a leg of a conventional Wheatstone bridge circuit. A useful low-compliant force sensor is available from Honeywell under the trade name FSL05N2C. The Honeywell force sensor has a 500-g range (4.9 N full scale), which is suitable for most of the screening methods described in subsequent sections. As noted earlier, many force sensors can tolerate only modest variation in temperature without compromising accuracy and precision. The use of a composite shaft 120 having an insulating sheathing 160, 162, 164 (FIG. 2) permits substantial temperature variation of the sample array 230 without significantly affecting the temperature and accuracy of the sensors 106.

In an alternative embodiment, force sensors are incorporated into the flexure strips 150 by placing strain gages on the diaphragms 166 (FIG. 2). Strain resulting from the application of a known force—typically a deadweight load applied to the rigid shaft 120—is recorded and used to develop a calibration curve for the force sensor. The principal disadvantage of this approach is the extensive signal conditioning requirements associated with strain gage measurements.

Referring again to FIG. 1 and FIG. 2, the PDMA 100 may include an environmental chamber (not shown) that encloses the sample holder 102, the probes 104, and the upper 152 or intermediate 154 segments of the isolation block modules 124. The chamber may be filled with a gas of known composition to study its influence on bulk physical properties of the sample array 230 elements. Or the chamber may be filled with an inert gas to reduce oxidation of the sample array 230 elements during screening. Generally, the annular gap 168 between the composite shafts 120 and the cylindrical apertures 122 is minimized to limit the flow of gas out of the isolation block modules 124. In addition, the flexures 150 in the annular gaps 168 restrict gas efflux from the isolation block modules 124.

Alternatively, the environmental chamber may comprise a substantially gas-tight enclosure that surrounds the sample holder 102, the probes 104, the isolation block modules 124, and the sensors 106. The enclosure may be further separated into two compartments—one that encloses the sample holder 102 and the material samples 230, and one that encloses the sensors 106 and the isolation block modules 124. The latter embodiment allows blanketing the sample holder 102 and material samples 230 with a first gas that is different than a second gas blanketing the sensors 106. In this way, the PDMA can vary the environment of the material samples 230 independently of the sensors 106, while maintaining the sensors 106 at conditions different than or the same as the laboratory environment.

The environmental chamber may include devices for regulating and/or monitoring the temperature of the sample array 230 elements. Useful devices include one or more heating or cooling elements placed within a gas stream that feeds the environmental chamber containing the sample array 230. Other useful devices include an array of radiant heaters positioned adjacent to the sample array 230. Alternatively, the PDMA 100 may include resistance heaters or thermoelectric devices that are attached to the sample holder 102, which heat or cool individual or groups of sample array 230 elements. The PDMA 100 may also include devices such as thermocouples, thermistors, or resistive thermal devices (RTD) for monitoring the temperature of individual sample array 230 elements. In some embodiments, the PDMA 100 includes a temperature controller, such as a data acquisition board, for subjecting the sample array 230 to a desired temperature-time profile. The temperature controller automatically adjusts the power supplied to the heating and cooling devices in response to signals received from the temperature monitoring devices. Typically, software running on an external computer communicates and coordinates functions of the temperature controller and the temperature monitoring devices.

PDMA Control and Data Acquisition

Figure 7:
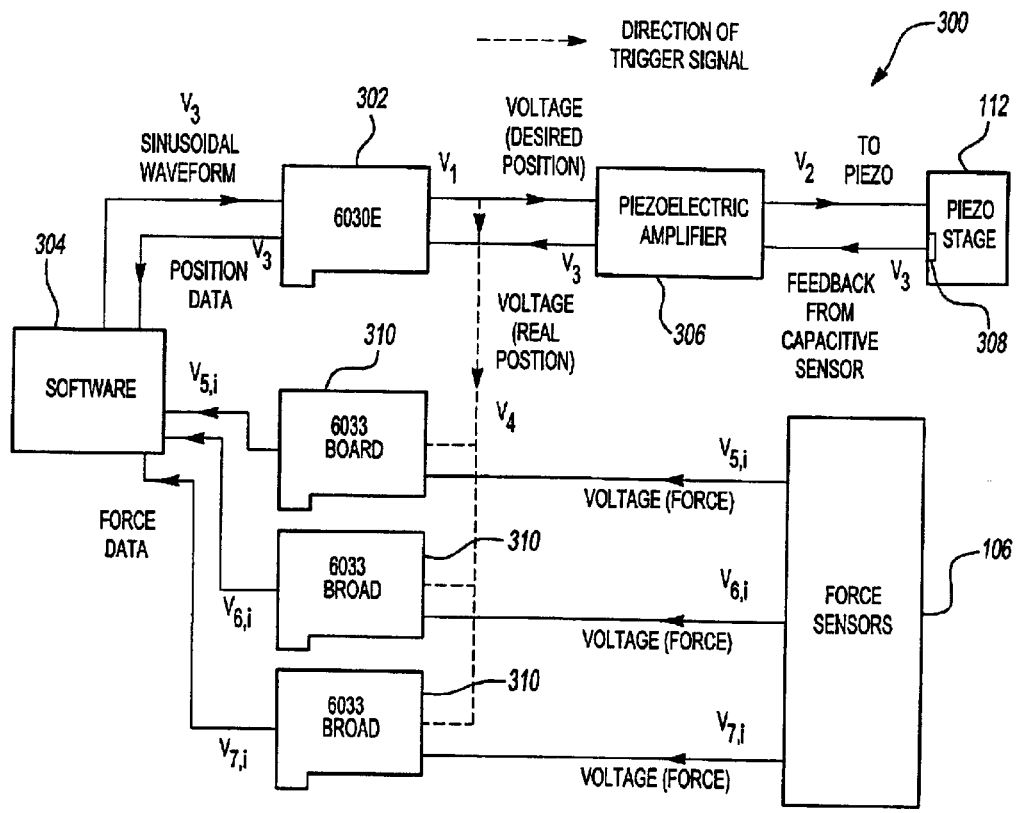
FIG. 7 is a flow chart for the data acquisition control.

FIG. 7 shows schematically a system 300 for data acquisition and control of the PDMA. As noted in the discussion of FIG. 1, the PDMA 100 includes first 110 and second 112 translation actuators for displacing the sample array 230 (FIG. 4) in a direction normal 114 to the probes 104. The first translation actuator 110 provides relatively coarse displacement of the sample holder 102; it positions the elements of the sample array 230 near the probe 104 test fixtures 118, and can be regulated using a DC motor controller (not shown). The second translation actuator 112 provides relatively fine displacement of the sample holder 102 and is responsible for carrying out mechanical perturbations of the sample array 230 elements.

The second translation actuator 112 shown in FIG. 7 comprises a piezoelectric translation stage. A primary data acquisition board 302 (e.g., National Instruments 6030E), which is located in an external computer 304, controls the operation of the second translation actuator 112. The primary board 302 generates a voltage, $V_1$, which is proportional to the desired displacement of the actuator 112 (and sample holder 102). This voltage is fed to a piezoelectric amplifier 306 that monitors the position of the actuator 112 via a capacitive position sensor 308. In response to $V_1$, the piezoelectric amplifier 306 varies the charge, $V_2$, which it supplies to the actuator 112 to move the sample holder 102 to its desired position. The position sensor 308 generates a voltage, $V_3$, which is read by the amplifier 306 and indicates the actual position of the second translation actuator 112.

As shown in FIG. 7, the primary data acquisition board 302 and the external computer 304, respectively, read and record $V_3$. In response to the value of $V_3$, the primary board 302 updates $V_1$ as necessary and generates a timing pulse, which triggers acquisition of $V_3$ from the position sensor 308, thereby synchronizing signals $V_1$ and $V_3$. The acquisition of $V_3$ also generates a second timing pulse, $V_4$, which triggers acquisition of voltages $V_{5,i}$, $V_{6,i}$, and $V_{7,i}$, from the sensors 106. Secondary data acquisition boards 310 acquire $V_{5,i}$, $V_{6,i}$, and $V_{7,i}$, where subscript "i" refers to a particular data line (channel) of the data acquisition board 310. Thus, measurements of the response of the sample array 230 to mechanical perturbations is synchronized with the motion of the second translation actuator 112 (and sample holder 102), and the measurement of the actuator 112 position. Although the system 300 shown in FIG. 7 uses three secondary data acquisition boards 310 having 32 channels each, the number of boards 310 will depend on the number of available data channels and sensors 106. Alternatively, the PDMA may use a single data acquisition board to control the actuator 112 position and to acquire sensor 106 data, assuming the board has a sufficient number of data channels and output signals.

Software running on the computer 304 coordinates the activities of the boards 302, 310 and allows the user to specify screening parameters including positions of the first 110 and second 112 translation actuators at any given time, the number of sample array 230 elements, and so on. Operation of the data acquisition and control system 300 with respect to specific physical property tests is discussed below.

Screening Methods, Sample Arrays and Holders, Probe Test Fixtures

The PDMA 100 of FIG. 1 is designed to screen material sample arrays 230 based on measurements of many different bulk physical properties. For example, the PDMA 100 can measure properties related to Young's modulus, which includes flexure, uniaxial extension, biaxial compression, and shear. The PDMA 100 can also measure physical properties of material samples 230 related to hardness (indentation), failure (stress and strain at failure, toughness), adhesion (tack, loop tack), and flow (viscosity, melt flow indexing, and rheology), among others.

As described in the next sections, the screening criteria or measurement techniques depend on selection and use of appropriate sample array 230 format, sample holder 102 configuration, and probe 104 test fixture 118 design. We use different reference numbers to distinguish between separate embodiments of the sample array 230, sample holder 102, probes 104 and test fixtures 118. For example, probe 104 test fixtures 118 shown generally in FIG. 1 are labeled 322 in FIG. 8 (flexure); 422 in FIG. 13 (uniaxial and biaxial compression); 462 in FIG. 14 (shear); 402 in FIG. 15 (indentation), 542 in FIG. 17 (viscosity and rheology); and the like.

Determination of Young's Modulus from Flexure Measurements—"Push-Pin Test"

Figure 8:
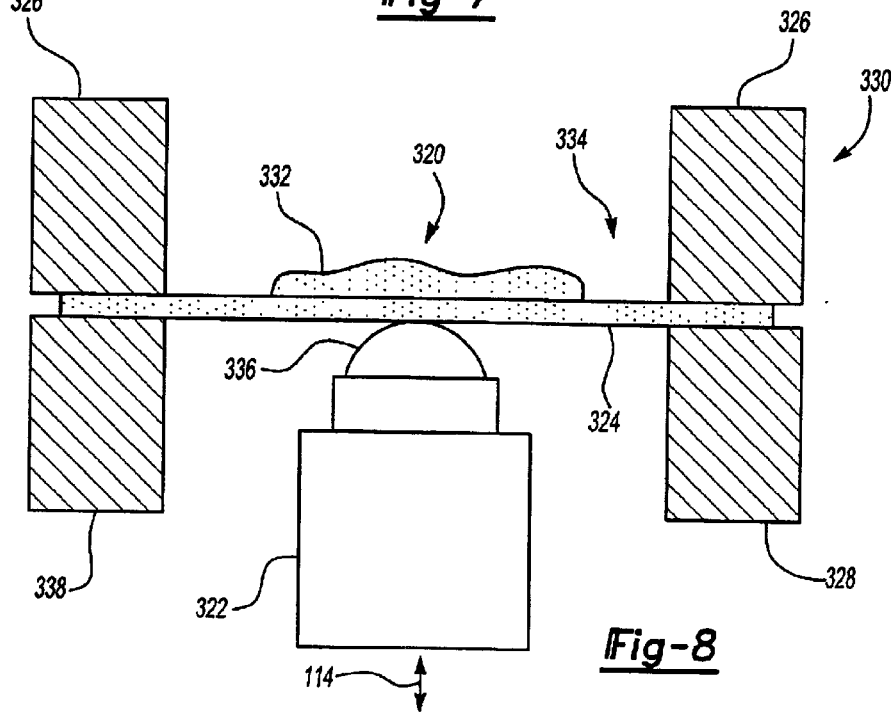
FIG. 8 shows a cross-section view of representative components of material sample array and test fixtures that the PDMA of FIG. 1 can use to screen libraries of materials based on flexure measurements.

FIG. 8 shows a cross-section view of representative components of a material sample array 320 and test fixtures 322 that the PDMA 100 can use to screen libraries of materials based on flexure measurements. The sample array 320 generally includes a flexible substrate 324 clamped between perforated plates 326, 328 that comprise a sample holder 330. One or both sides of the flexible substrate 324 are coated with material samples 332 at discrete, predefined regions on the substrate 324. The predefined regions generally correspond to unclamped portions of the flexible substrate 324, which in FIG. 8, coincide with circular perforations 334 in the plates 326, 328. Each of the test fixtures 322 has a hemispherical end 336 of known radius that contacts the sample array 320 over a surface area that is substantially less than the unclamped area of the flexible substrate 324. Useful substrate 324 materials include polyimide films, which generally range in thickness from about $10^1$ $\mu$m to about $10^2$ $\mu$m. The material samples 332 have comparable thickness, and are typically twenty $\mu$m or so thick.

In some cases, clamping may be insufficient to secure the flexible substrate 324 between the perforated plates 326, 328. Thus, in an alternative embodiment, the flexible substrate 324 is bonded to one of the perforated plates 326, 328 using a pressure sensitive adhesive. The adhesive should be less compliant than the flexible substrate 324, and during its application, care should be taken to ensure a uniform bond line adjacent to the circular perforations 334. Washers or similar shim stock (not shown) can be used to define a standoff between the two perforated plates 326, 328.

Various methods can be used to make the sample arrays 320. For example, a sample array 320 comprised of polymers can be prepared by depositing known amounts of solid samples 332 at predefined regions on the flexible substrate 324. Following deposition, the samples 332 and substrate 324 are compressed under melt-flow conditions to create polymer films of requisite thickness. Alternatively, the polymer samples 332 can be dissolved in one or more solvents and deposited at predefined regions on the flexible substrate 324 using conventional liquid handling techniques such as automated pipetting. To prevent liquid samples 332 from spreading beyond their respective predefined regions, the flexible substrate 324 is pretreated—e.g., by selective etching or by silane treatment—to modify the surface energy of the substrate 324 in or out of the predefined regions. See, for example, co-pending U.S. Patent Application entitled "Formation of Combinatorial Arrays of Materials Using Solution-Based Methodologies," Ser. No. 09/156,827, filed Sep. 18, 1998, and co-pending U.S. Patent Application, "Polymer Libraries on a Substrate, Method for Forming Polymer Libraries on a Substrate and Characterization Methods With Same," Ser. No. 09/567,598, filed May 10, 2000, all of which is herein incorporated by reference. Upon deposition, the liquid samples 332 are confined to regions having like surface energies, and form solid films following evaporation of the solvent. After brief annealing under vacuum to remove residual solvent, the thickness at the center of each sample 332 can be measured using a variety of known techniques, including optical reflection profilometry and optical interference profilometry. Finally, metallic or organometallic compounds can be directly deposited on the flexible substrate 324 by chemical vapor deposition, physical vapor deposition, or similar techniques.

In some instances, the size and placement of the material samples 332 on the flexible substrate 324 can affect the physical measurements. For example, as shown in FIG. 8, each of the material samples 332 covers a substantial portion but not all of the substrate 324 delineated by the circular perforations 334 in the sample holder 330 plates 326, 328. Although films made by solution deposition techniques often have relatively uniform thickness near their centers, they exhibit substantial variation away from their centers, which can influence flexural measurements. To minimize edge effects, material samples 332 made by solution deposition techniques should generally extend beyond the regions defined by the circular perforations 334. In addition, the material samples 332 shown in FIG. 8 are typically deposited on one side of the substrate 324, and generally on the side of the substrate 324 facing away from the test fixtures 332. This helps eliminate forces resulting from adhesion between the test fixtures 322 the samples 332 and from plastic deformation of the samples 332 at the contact points between the test fixtures 322 and the sample array 320. Samples 332 may be located on the side of the flexible substrate 324 facing the test fixture 322 as long as plastic deformations are unlikely or combined measurements of adhesion and flexural modulus are desired.

Figure 9:
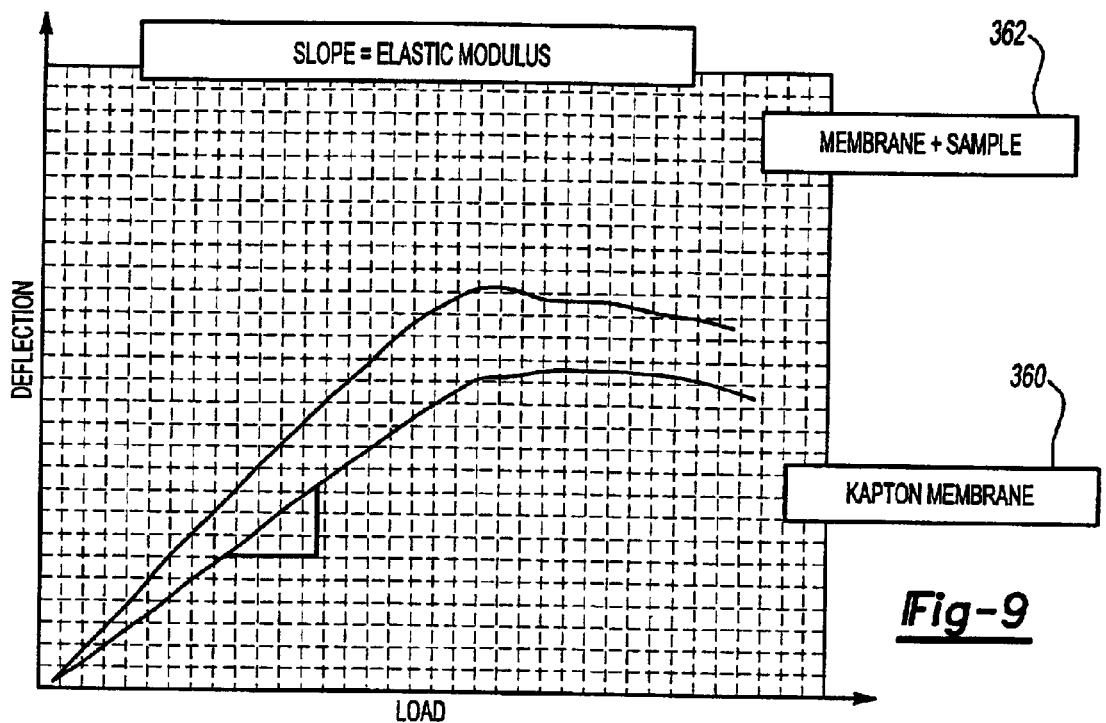
FIG. 9 shows typical results of a flexure measurement for a single element of a material sample array.

FIG. 9 shows results of a flexure measurement for a single element of the material sample array 320 shown in FIG. 8.

Flexure measurements or "push-pin" tests, generally comprise translating the sample holder 330 and material sample array 320 in a direction 114 normal to a plane containing the flexible substrate 324, and recording the force exerted on the test fixtures 322 as a function of the displacement of the array 320 (or second translation actuator 112). An analysis of the resulting force-displacement curve 360 in the absence of a material sample 332 coating yields the elastic modulus, $E_1$, of the substrate 324. Comparison of force-displacement curves 362, 360 obtained with and without the coating yields the ratio of the sample 332 elastic modulus, $E_2$, to the substrate 324 elastic modulus. As described below, the analysis of the force-displacement curves employs well-known analytical and numerical models for the behavior of a clamped membrane.

Figure 10:
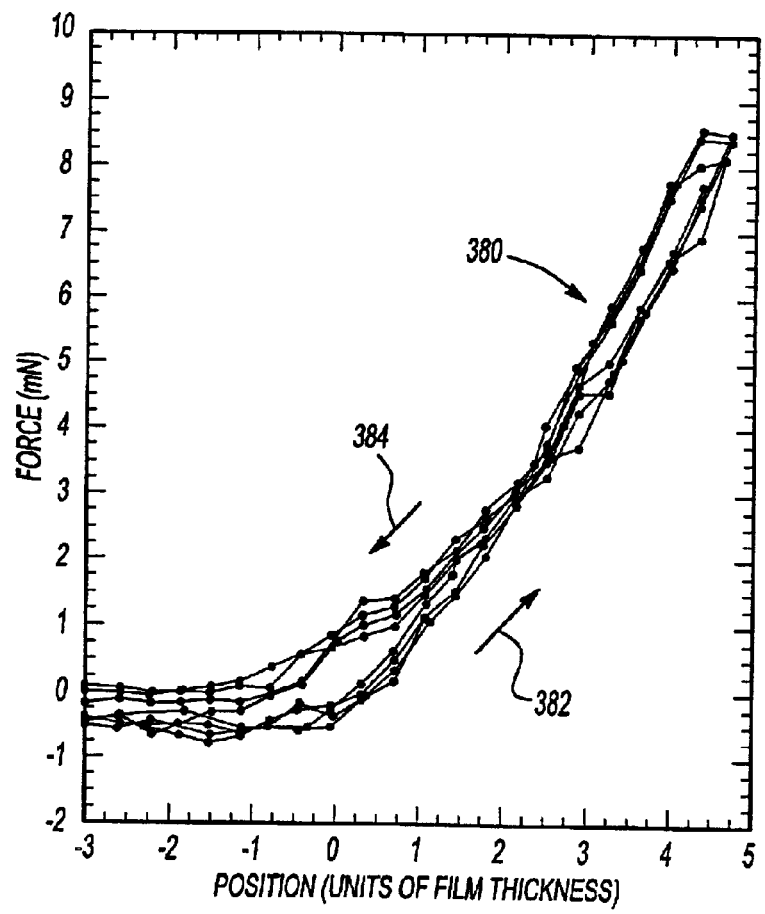
FIG. 10 shows typical results of flexure measurements made in a "direct" mode.
Figure 11:
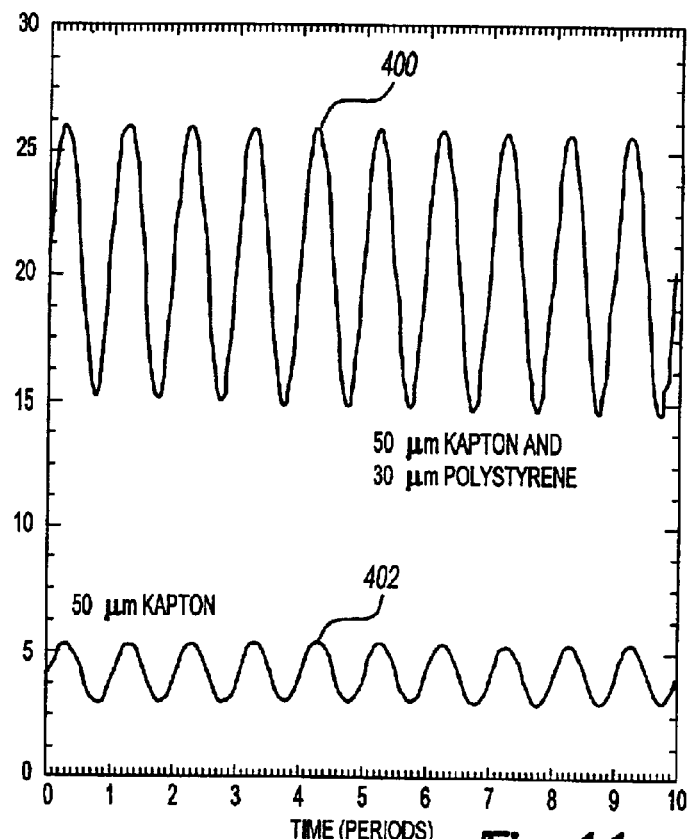
FIG. 11 shows typical results of flexure measurements made in an "oscillatory" mode.

FIG. 10 and FIG. 11 show, respectively, results of flexure measurements made in a "direct" mode or an "oscillatory" mode. In terms of the PDMA components shown in FIG. 8, the direct mode comprises initially translating the sample holder 330 and material sample array 320 against the test fixtures 322 at a known rate until the sample 332 reaches a given maximum deflection or normal 114 displacement. The method includes reversing the displacement until the sample 332 returns to its original position, and analyzing the resulting force-displacement curve to characterize the mechanical properties of the sample 332. FIG. 10 shows representative force-displacement curves 380 for the initial 382 and return 384 displacements of 13.7 $\mu$m thick polyimide (KAPTON) films undergoing strain rates ranging from 25 $\mu$m/s to 250 $\mu$m/s. As expected, the force-displacement curves 380 are independent of strain rate.

Like the direct measurements, the oscillatory mode comprises translating the sample holder 330 and material sample array 320 against the test fixtures 322 at a known rate until the sample 332 reaches a given maximum deflection or normal 114 displacement. However, following the initial displacement, the method includes translating the sample holder 330 and sample array 320 along the deflection direction 114 in an oscillatory motion of known amplitude and frequency. As described in detail below, the amplitude and initial displacement are typically chosen to ensure that, throughout the entire motion, the sample 332 or substrate 324 deflections remain in a linear deflection regime defined below.

FIG. 11 shows oscillatory force-displacement curves 400, 402 for, respectively, a 50 $\mu$m thick polyimide (KAPTON) substrate 324 with and without a 30-$\mu$m thick polystyrene coating (sample 332). The oscillatory technique yields frequency-dependent modulus values that for some samples 332 relate to characteristic modes of molecular deformation. Thus, the oscillatory technique is often called "dynamic mechanical spectroscopy" because it is analogous to conventional spectroscopic measurements, which identify characteristic frequencies of electronic transitions. One advantage of the oscillatory technique over the direct method is that, if the measurements are performed in the linear deflection regime, the force-displacement curve is also sinusoidal, exhibiting the same frequency as the test fixture 322 or probe deflection. As a result, the effective bandwidth of the measurement is comparatively low, and the associated signal-to-noise ratio is comparatively high.

To measure modulus using the oscillatory method, the sample holder 330 is attached to the second translation actuator 112, and the test fixtures 322 are attached to the probes 104. The first (coarse) translation actuator 110 positions the sample holder 330 near the probes 104, but at a sufficient distance so that none of the test fixtures 322 contact the flexible substrate 324 or any elements 332 of the sample array 320. Using the second translation actuator 112, the PDMA 100 makes initial stiffness measurements (force per displacement amplitude) of the sample array 320 elements 332. Next, the first actuator 110 translates the sample holder 330 closer to the test fixtures 322 by a predetermined amount—typically, a step size of one half of the oscillatory displacement amplitude used in measuring stiffness—and the PDMA 100 repeats the stiffness measurements. The PDMA 100 continues this process until all of the material samples 332 of the array 320 are in contact with the test fixtures 332.

Figure 12:
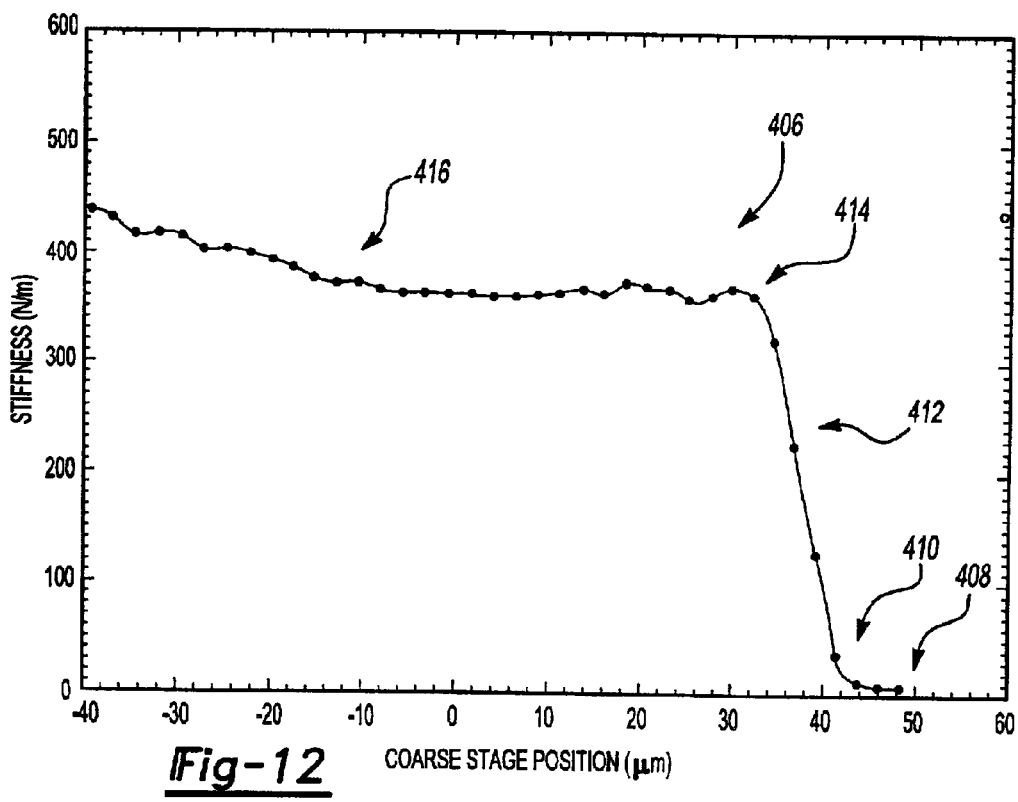
FIG. 12 shows a graph of stiffness versus displacement of the first translation actuator (coarse stage).

The stiffness measurements can be understood by reference to FIG. 7 and FIG. 12. Referring first to FIG. 7, software running on the computer 304 directs the primary data acquisition board 302 to generate a sinusoidally varying output voltage, $V_s$. The output voltage corresponds to a typical second translation actuator 112 oscillation amplitude of, for example, five $\mu$m, at a fixed frequency (e.g., ten Hz) and for a fixed number of cycles (e.g., sixty six). The amplitude of oscillation is chosen so as to produce a reasonably large signal at the sensors 106 for the samples 332 of interest. The first two waveforms are usually discarded to eliminate transients. The remaining data are Fourier transformed to extract the actual amplitude of the oscillation of the second translation actuator 112 (or sample holder 330) and the amplitude of the force recorded by the sensors 106 at the drive frequency. Dividing the force amplitude by the motion amplitude yields the stiffness (N/m). The raw data for each sensor 106 may also be cross-correlated against the raw data for the actual second translation actuator 112 motion in to extract the relative phase of the two signals. This phase serves as a measure of the character of the deformation (elastic versus viscous) and can be used to separate the measured stiffness into an elastic or storage contribution and a viscous or loss contribution.

FIG. 12 shows a representative stiffness-displacement 406 curve measured at a drive frequency of ten Hz, an oscillation amplitude of 5 $\mu$m, and a coarse stage (first translation actuator 11) displacement step size of 2.5 $\mu$m. The material sample 332 is a thin film of a polystyrene-poly(ethene-co-butene)-polystyrene block copolymer, which has been deposited on a 0.002-inch thick polyimide flexible substrate 324. At the beginning of the modulus measurements, as represented by a first region 408 of the stiffness-displacement curve 406, the probes 104 are not in contact with the material samples 332. In this region of the curve 406, the sensors 106 record only electrical noise during oscillation of the second translation actuator 112, and the resulting measured stiffness is low (e.g., less than about ten N/m). As the test fixtures 322 of the probes 104 are brought into contact with the sample array 320, the sensors 106 initially see a periodic but non-sinusoidal signal at the drive frequency. This phenomenon is represented by a second region 410 of the stiffness-displacement curve 406, and corresponds to contact between the probe and sample 332 at the maximum oscillation amplitude of the second translation actuator 112. Fourier transforms of these signals show a number of higher order harmonics that may be used to identify the point at which, for a given probe 106 and sample 332, the test fixture 322 first contacts the sample array 320 element 332. Upon further movement of the first translation actuator 110 (and sample holder 330), the signals from the sensors 106 become increasingly sinusoidal; Fourier transforms of these signals show decreasing levels of higher order harmonics. Along this third region 412 of the stiffness-displacement curve 406, the measured stiffness increases with displacement of the first translation actuator 110 and the sample holder 330.

Eventually, the probes 106 are in contact with the material samples 332 throughout the oscillation of the second translation actuator, as represented by a fourth region 414 of the stiffness-displacement curve 406. Here, the output signals from the sensors 106 are almost purely sinusoidal, and the stiffness becomes independent of the position of the first translation actuator 110. In this region 414 of the curve 406—the "linear deflection regime"—the force exerted by a given sample 332 is a linear function of the oscillation amplitude of the second translation actuator 112. Also, in this region 414 of the stiffness-displacement curve 406, the substrate 324 modulus and the material sample 332 modulus can be calculated using analytical models that describe the deflection of a circular membrane clamped along its circumference. See discussion of equations I–IX below.

The width of the region 412 of the stiffness-displacement curve 406 in which the stiffness rises rapidly with displacement, is approximately equal to twice the amplitude of the oscillation of the second translation actuator 112. Thus, using a first (coarse) actuator 110 step size of one half the oscillation amplitude ensures at least four data points throughout this region and provides a reasonably accurate estimate of the sample 332 stiffness at the edge of the linear deflection regime ("linear stiffness"). To bring all of the samples 332 into contact with the test fixtures 332, it may be necessary to drive the first actuator 110 to a position in which some samples 332 are in a fifth region 416 of the stiffness-displacement curve 406. This region 416 of the curve 406 is outside of the linear deflection regime 414 and exhibits a rise in the sample stiffness with increasing displacement of the first translation actuator 110.

The PDMA automatically determines linear stiffness for each stiffness-displacement curve 406 of the material samples 332 by starting from the initial first translation actuator 110 position and identifying the first stiffness measurement that exceeds a predetermined threshold value (e.g., twenty five N/m). Once this threshold is crossed, the stiffness measured 2A/C+1 steps later, where A is the oscillation amplitude of the second actuator 112 and C is the first (coarse) translation actuator 110 displacement, is assumed to be equal to the linear stiffness and is recorded.

The moduli of the substrate 324 and the material samples 332, can be obtained from the force-displacement curves 360, 362, 400, 402 using analytical models that describe the deflection of a circular membrane clamped along its circumference. For deflections of up to about one-half of the thickness of the circular membrane—the linear deflection regime—the deflection, y, is given by the expression:

$$y = -\frac{Fr^2}{16\pi D},$$  I $$D = \frac{E\delta^3}{12(1-v^2)},$$  II where E is the modulus of the clamped film or membrane, r is the radius of the film, δ is the thickness of the film, F is the force resulting from the deflection, v is Poisson's ratio, which is often assumed to be of order 0.3, and D is the plate constant. See W. C. Young, *Roark's Formulas for Stress and Strain* (1989). For larger film displacements, the deflection is approximated by:

$$\frac{Fr^2}{E\delta^4} = k_1\left(\frac{y}{\delta}\right) + k_2\left(\frac{y}{\delta}\right)^2,$$  III where $k_1$ and $k_2$ are constants that depend on the ratio of the area of test fixture 322 contact to the area of the clamped film 324. Values of these constants have been tabulated for a wide range of area ratios. Depending on the relative magnitudes of the deflection and film thickness, equations I–III yield the substrate 324 modulus, $E_1$, for values of F and y from the force-displacement curves 360, 362, 402.

Given the modulus of the substrate 324, one may obtain the modulus of the samples 322 from analytical models that describe the deflection of a composite circular film or plate clamped along its circumference. The plate constant D for a composite plate formed from two materials having moduli $E_1$ and $E_2$, and thickness $\delta_1$ and $\delta_2$, is given by:

$$D = KD_1.$$  IV

In the expression for D, $$K = 1 + \varepsilon\tau^3 + \frac{3(1+\tau)^2}{1+1/\varepsilon\tau},$$  V $$\varepsilon = \frac{E_1}{E_2}, \text{ and}$$  VI $$\tau = \frac{\delta_1}{\delta_2}.$$  VII If subscripts "1" and "2" in equations IV–VII refer to the sample 332 and substrate 324, respectively, and if $f=F_2/F_1$ represents the ratio of forces measured at the same deflection y for the coated and non-coated substrates, then for small deflections described by equations I and II, equation V becomes:

$$f = 1 + \varepsilon\tau^3 + \frac{3(1+\tau)^2}{1+1/\varepsilon\tau}.$$  VIII

Expanding equation VIII and collecting like-terms yields:

$$(\varepsilon\tau)^2\tau^2+(\varepsilon\tau)(4\tau^2+6\tau+4-f)+(1-f)=0.$$  IX

Since τ, f and $E_1$ are known, equation IX can be solved for ε, and $E_2$ can be calculated from equation VI.

Other embodiments of the flexure measurements include: (i) omitting the coating if the mechanical properties of the flexible substrate are of interest, as would be the case for freely standing metal films; (ii) replacing the circular substrate 324 with a rectangular beam or other structure of known geometry; and (iii) relaxing the constraint that each of the test fixtures 322 has a hemispherical end 336 that contacts the sample array 320 over a surface area that is substantially less than the unclamped area of the flexible substrate 324.

Young's Modulus—Uniaxial Extension and Biaxial Compression

Figure 13:
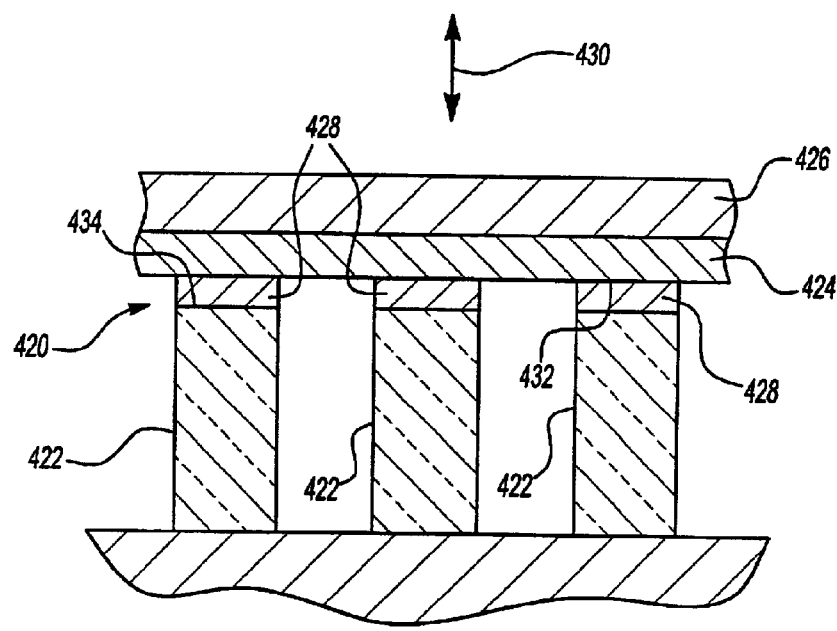
FIG. 13 shows a cross-section view of a portion of a material sample array and test fixtures that the PDMA can use to screen libraries of materials based on uniaxial extension or biaxial compression measurements.

FIG. 13 shows a cross-section view of a portion of a material sample array 420 and test fixtures 422 that the PDMA 100 can use to screen libraries of materials based on uniaxial extension or biaxial compression measurements. The sample array 420 generally includes a rigid substrate 424 that is attached to a moveable sample holder 426. Discrete material samples 428 belonging to a library of materials are sandwiched between the rigid substrate 424 and the test fixtures 422. If measuring tensile forces resulting from uniaxial extension, the material samples 428 are bonded to the rigid substrate 424 and the test fixtures. Using the second translation actuator 112, the sample holder 426, rigid substrate 424, and sample array 420 are translated away from the test fixtures 422 in a direction 430 normal to a plane containing the material sample array 420. During the translation, the PDMA 100 records tensile forces exerted on the test fixtures 422 at the sensors 106 as a function of displacement from the sample array 420.

When measuring biaxial compression, the material samples 428 of FIG. 13 are not bonded to the rigid substrate 424 and the test fixtures 422. Instead, the samples 428 will flow laterally when compressed. Surfaces 432, 434 of the substrate 424 and test fixtures 422 that contact the material samples 428 have low coefficients of friction and are designed to minimize sample deformation associated with friction. The substrate 424 and the test fixtures 422 may be fabricated from a low friction material such as a fluoropolymer, or their surfaces 432, 434 may be coated with lubricating oil. In preferred embodiments, the surface 434 of each test fixture 422 is generally smooth, flat, axisymmetric, and has a diameter comparable to the diameter of the material sample 428. In a representative measurement, the test fixtures 422 and the sample array 420 are brought into contact by the first translation actuator 110, and the second translation actuator 112 compresses the material samples 428 at a defined displacement rate while the sensors 106 measure forces exerted on the test fixtures 422. In an alternative embodiment, the second translation actuator 112 compresses the material samples 428 sinusoidally at a known amplitude and frequency, while the sensors 106 measure the compressive forces on the test fixtures 422. Comparison of the force and displacement waveforms yields the complex compressive modulus of the material samples 428 at that frequency. Note that compressive measurements at small strains are not limited to solids, but can be performed on viscoelastic liquids as well. The resulting waveforms yield the biaxial extensional modulus of the liquid samples 428.

Young's Modulus—Shear

Figure 14:
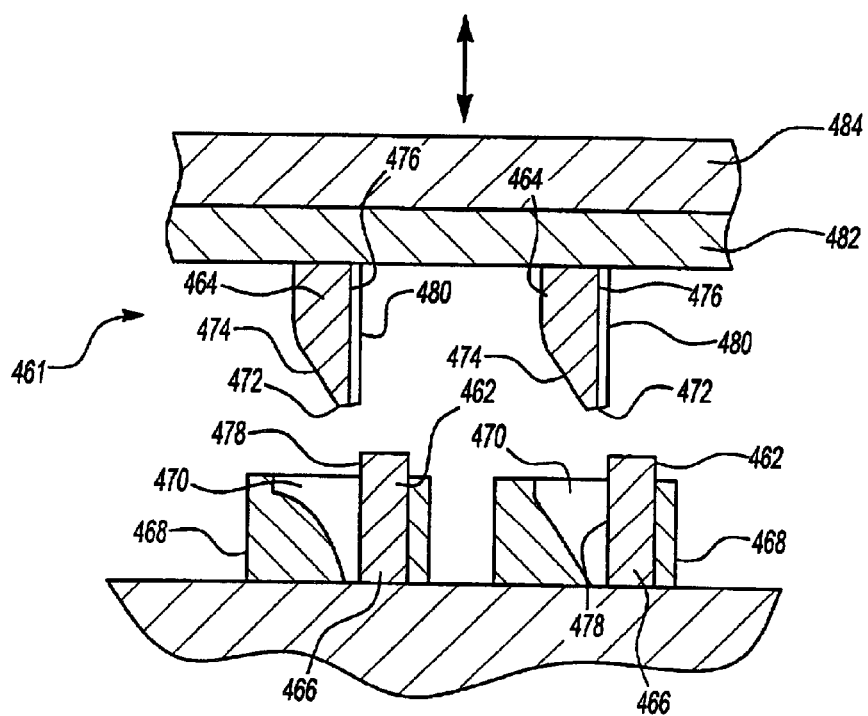
FIG. 14 shows a cross-section view of representative components of material sample array and test fixtures that the PDMA of FIG. 1 can use to screen libraries of materials based on shear force measurements.

FIG. 14 shows a cross-section view of representative components of a material sample array 460 and test fixtures 462 that the PDMA 100 of FIG. 1 can use to screen libraries of materials based on shear force measurements. Each element 464 of the sample array 460 and corresponding test fixture 462 comprise portions of a cylinder that has been bisected along a plane containing its symmetry axis. The base 466 of the test fixture 462 is contained within a cylindrical cup 468 having a tapered recess 470 positioned parallel to, but displaced from, the cylinder (test fixture 462) axis. The tip 472 of the sample array 460 element 464 is formed into a tapered pin 474 that mates with the tapered recess 470. Inserting the pin 474 into the recess 470 brings the rectangular faces 476, 478 of each sample array element 464 and test fixture 462 together, thereby compressing and shearing material samples 480 present on the faces 476, 478. The sample array elements are bound to a rigid plate 482, which is attached to a moveable sample holder 484. The material samples 480 may be formed into sheets of desired dimensions, which are laminated to one or both faces 476, 478 prior to measurement. Alternatively, the samples 480 may be dissolved in a solvent and deposited on one or both of the faces 476, 478 by standard liquid handling techniques. Following evaporation of the solvent, the samples 480 are compressed between the faces 476, 478 of the test fixture 462 and the sample array element 464. A typical measurement comprises displacing the sample array 460 relative to the test fixtures 462 in a direction 486 parallel to their faces 476, 478, while measuring the resulting shear forces on the test fixtures 462. Alternatively, the second translation actuator 112 can execute a sinusoidally varying displacement of the sample array 460, while measuring amplitudes and relative phases of the resulting shear forces on the test fixtures 462. Such measurements can yield Young's modulus, rheological modulus, and adhesion characteristics. In a closely related test, the PDMA can measure, for a given force, the time required for adhesive or cohesive failure of material samples 480.

Young's Modulus and Hardness—Identation

Figure 15:
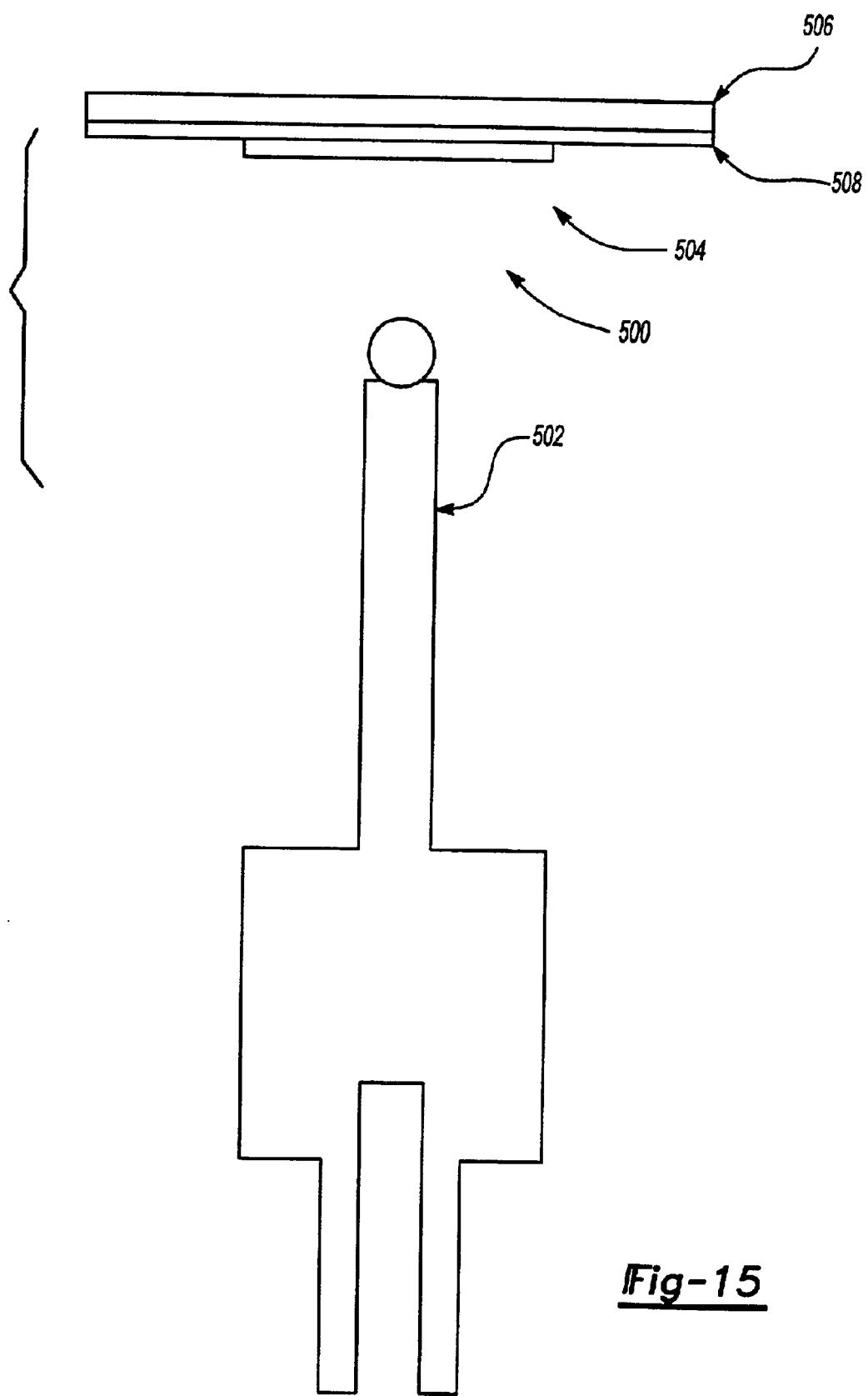
FIG. 15 shows a cross-section view of a portion of a material sample array and a representative test fixture that the PDMA of FIG. 1 can use to screen libraries of materials based on indentation measurements.

FIG. 15 shows a cross-section view of a portion of a material sample array 500 and a representative test fixture 502 that the PDMA of FIG. 1 can use to screen libraries of materials based on indentation measurements. In a typical indention measurement, the force required to drive the test fixture 502 a known distance into a material sample 504 is measured by the sensors 106 and related to various properties of the material sample 504. The resulting deformation generally involves both plastic and elastic components, which complicates the analysis. The analytical difficulties generally limit the use of the technique to index measurements, where material samples 504 are ranked based on the penetration forces for a given displacement speed and penetration depth. Although the samples 504 may be mounted on a flexible substrate such as polyimide, the penetration force will include a contribution from the deformation of the substrate. Thus, the samples are generally disposed on a rigid substrate 506, such as aluminum or stainless steel, which is attached to a moveable sample holder 508. Each of the test fixtures 502 may be a stainless steel hemisphere of known diameter, a stainless steel stylus (pointed tip) of known opening angle, or a flat-topped cylindrically symmetric rod.

Figure 16:
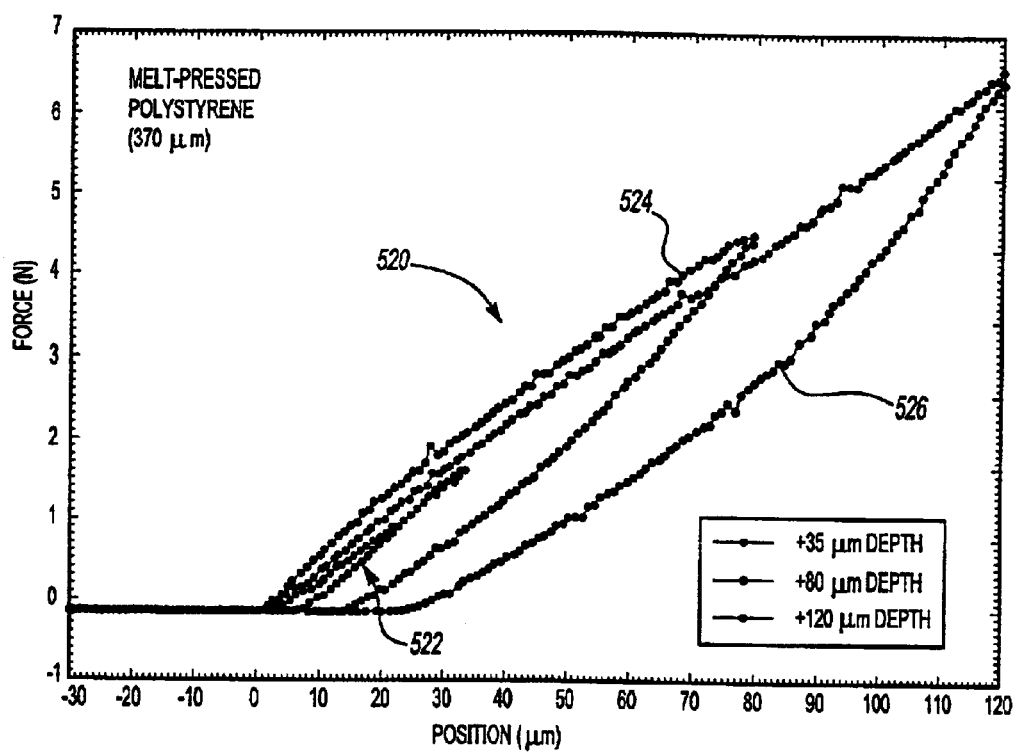
FIG. 16 shows force-displacement curves for indentation measurements of melt-pressed polystyrene samples mounted on a rigid substrate.

FIG. 16 shows force-displacement curves 520 for melt-pressed polystyrene samples mounted on a rigid substrate. The three curves 522, 524, 526 represent force-displacement profiles for penetration depths of 35 $\mu$m, 80 $\mu$m, and 120 $\mu$m, respectively. Although the force-displacement curves are somewhat reproducible for small deformations, plastic deformation appears at about ten percent of the sample thickness.

Viscosity

Figure 17:
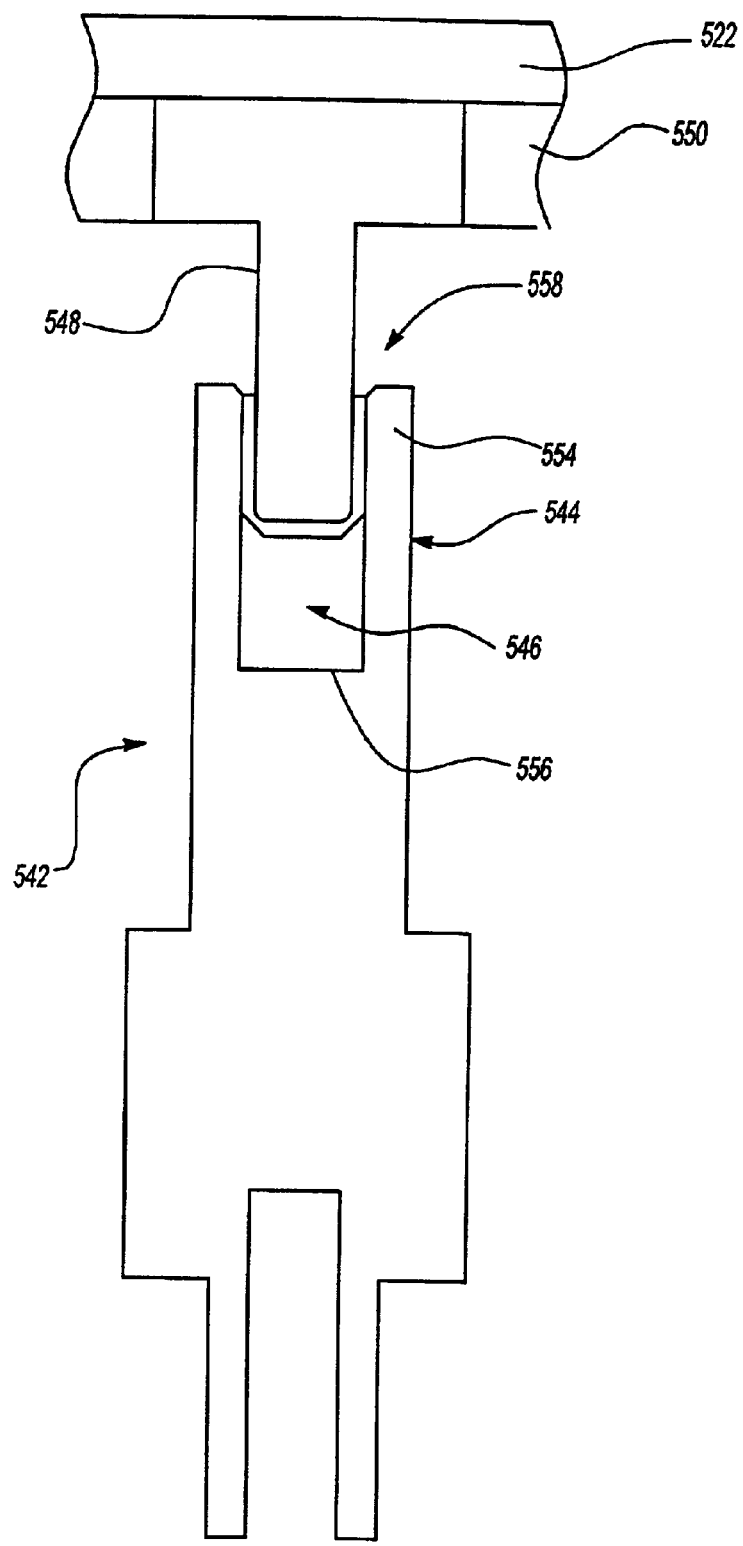
FIG. 17 shows a cross-sectional view of a portion of a material sample array and a representative test fixture that the PDMA of FIG. 1 can use to screen libraries of materials based on viscosity or viscosity-related measurements.

FIG. 17 shows a cross-sectional view of a portion of a material sample array 540 and a representative test fixture 542 that the PDMA 100 of FIG. 1 can use to screen libraries of materials based on viscosity-related measurements. Generally, the driving force necessary to move a body of known size, shape and surface texture through a liquid at a given relative velocity will provide a measure of viscosity. However, whether the force measurement can be related to the viscosity of the liquid depends strongly on the complexity of the flow field induced by the relative motion.

Since the embodiment shown in FIG. 17 produces a relatively simple flow field, it can yield an accurate measurement of viscosity. Each test fixture 542 generally comprises a cylindrically symmetric well 544 that contains a liquid sample 546. In addition to the liquid samples 546, the material sample array 540 includes spaced-apart cylindrical rods 548 having axes substantially aligned with the symmetry axes of the wells 544. The cylindrical rods 548 are attached to a rigid plate 550, which is mounted on a moveable sample holder 552. For each test fixture 542, the ratio of the well 544 depth to the well 544 radius is generally much greater than unity. As a result, the relative displacement of the rods 548 and wells 544 induces flow that is dominated by the motion of the liquid sample 546 within an annular gap 554 formed between the rod 548 and well 544—not by flow around the end of the rod 548. A viscosity measurement includes using the second translation actuator 112 to insert the rods 548 into the wells 544 at a constant rate, and measuring the forces on the test fixtures 542 at the sensors 106. This displacement may be reversed, in which the sensors 106 measures the force required to remove the rods 548 from the wells 544 at a constant displacement rate.

In a closely related second embodiment, each of the test fixtures 542 includes a through-hole (not shown), centered on the bottom 556 of each of the wells 544. The through-hole has a diameter much less than the diameter of the wells 544. Instead of the cylindrical rod 548 shown in FIG. 17, the second embodiment includes thin wires, polymer fibers, or other cylindrical filaments (not shown) having diameters less than the diameter of each through-hole. One end of each filament is attached to the rigid plate 550, while the other end passes through the through-holes in the bottom 556 of the wells 544. Typically, the end of the filament located adjacent the through-hole is left "free," provided the filament has sufficient flexural stiffness to remain substantially aligned with the well 544 axis. If lacking the requisite stiffness, the filaments are constrained by threading them through a small diameter clearance holes in plates (not shown) located adjacent the test fixtures 542. The wells 544 are filled with a high viscosity liquid such as a polymer melt; viscous entrainment of the liquid and surface tension are sufficient to contain the liquid within each well 544. To perform viscosity measurements, the second translation actuator 112 draws filaments through the through-holes at a constant rate and the sensors 106 measure forces exerted on the test fixtures 542 (wells 544). The length of the filament is generally greater than the depth of the well so that a steady-state velocity profile can be achieved in the through-hole. Compared to the first embodiment, this method simplifies sample preparation for high viscosity liquids, and generates results more applicable to common industrial processes such as fiber, band, and sheet coating.

Figure 18:
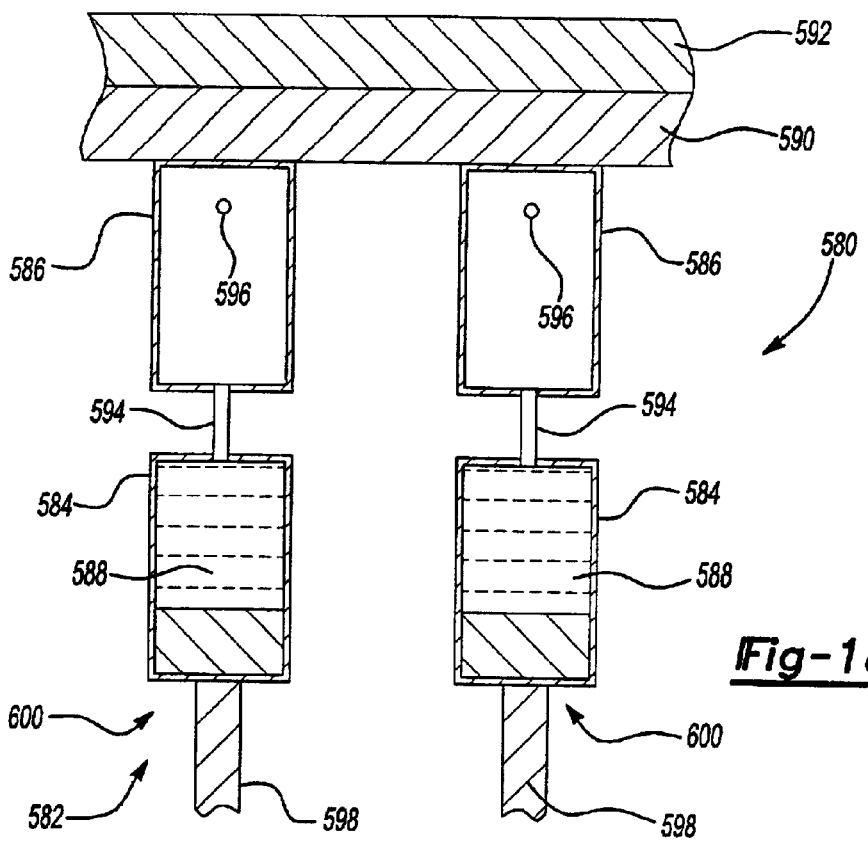
FIG. 18 shows a cross-sectional view of a portion of a material sample array and representative test fixtures that the PDMA of FIG. 1 can use to screen libraries of materials based on melt flow indexing.

FIG. 18 shows a cross-sectional view of a portion of a material sample array 580 and representative test fixtures 582 that the PDMA 100 of FIG. 1 can use to screen libraries of materials based on melt flow indexing. The sample array includes first 584 and second 586 cylindrical reservoirs, and liquid samples 588 that are initially contained in the first reservoirs 584. The second reservoir 586, which has slightly larger volume than the first reservoir 584, is attached to a rigid plate 590 that is mounted on a moveable sample holder 592. A cylindrical tube 594 having an inner diameter much less than the diameters of the first 584 and second 586 reservoirs provides fluid communication between the two reservoirs 584, 586. In addition, vent holes 596 located adjacent the rigid plate 590 provide fluid communication between the second reservoirs 586 and the atmosphere. The test fixtures 582 include pistons 598 inserted in open ends 600 of the first reservoir 584. Each of the pistons 598 have diameters that closely match the inner diameter of the first reservoir 584, which ensures a liquid-tight seal between the piston 584 and the first reservoir 584.

Screening based on melt flow indexing includes displacing the sample array 580 and sample holder 592 toward the pistons 598 at a constant rate using the second translation actuator 112, which forces the liquid samples 588 through the cylindrical tubes 594 into the second reservoir 586. The screening method also includes measuring and recording the forces exerted on the test fixtures 582 (pistons 598) at the sensors 106 while the liquid samples 588 flow through the cylindrical tubes 594. If one neglects friction between the pistons 598 and the walls of the first reservoirs 584, the viscosity, η, at a given shear rate can be determined from the Hagen-Poiseulle expression for laminar flow in a cylindrical tube:

$$Q = \frac{\pi d^4 \Delta P}{128 l \eta} \qquad \text{X}$$

where Q is the volumetric flow rate, d and l are the inner diameter and length of the cylindrical tube 594, and ΔP is the pressure drop across l. In equation X, Q is the product of the displacement rate and the cross sectional area of the first reservoir 584; ΔP is approximately the measured force divided by the cross sectional area of the first reservoir 584.

Rheology

The sample array 540 and test fixtures 542 shown in FIG. 17 also can be used to measure rheological (flow) characteristics of complex fluids. The sample array 540 includes cylindrical rods 548 or stainless steel pins of known length and diameter that have been coated with a viscous fluid sample 546. The test fixture 542 is comprised of a hollow cylinder or well 544, which has an inner diameter that varies with axial distance. Near the bottom 556 of the well 544, the inner diameter is substantially greater than the outer diameter of the stainless steel pin 548; near the open end 558 of the well 544, the inner diameter is slightly larger than the outer diameter of the pin 548. Within the well 544, the transition from small to large inner diameter is abrupt, and the length of the small diameter region is known.

Rheological measurements using the PDMA 100 of FIG. 1 generally comprises using the first translation actuator 110 to insert the pin into the well 544 sufficiently far so the fluid sample 546 coats the length of the small diameter region of the well 544. The method also includes translating the material sample array 540 (sample holder 552) sinusoidally using the second translation actuator 112, which shears the fluid sample 546 confined in the annular gap 554 between the pin 548 and the cylindrical well 544. During the shearing, the sensors 106 measure the forces exerted on the test fixtures 542. Knowing the dimensions of the pin 548 and the well 544, one can relate the relative amplitude and phase of the resulting force-time waveforms to the complex viscoelastic modulus of the fluid, G.

Figure 19:
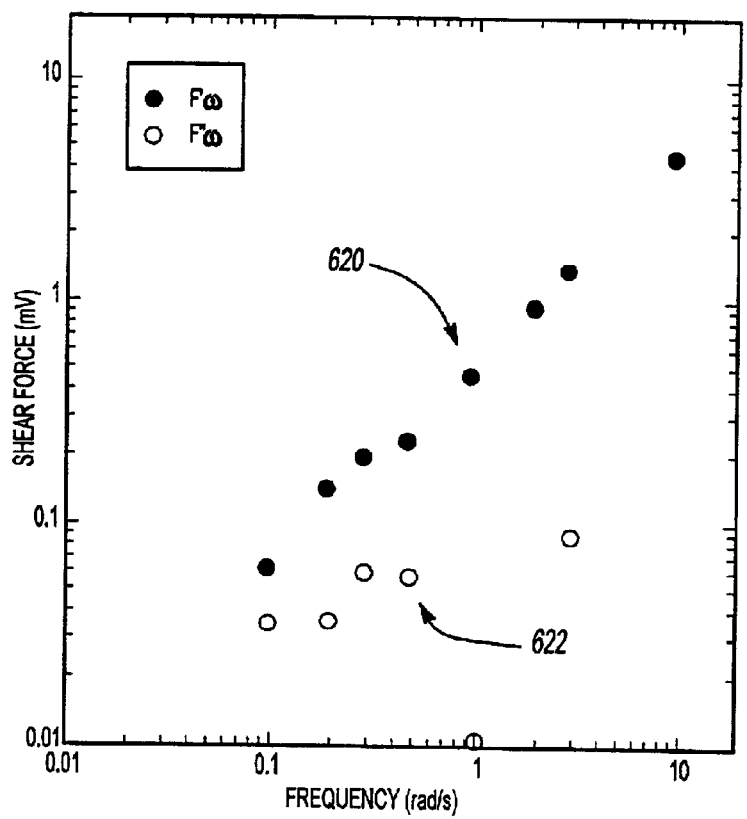
FIG. 19 shows real and imaginary parts, $F'(\omega)$ and $F''(\omega)$, of the force exerted on test fixtures by fluid motion of a polyisobutylene sample.
Figure 20:
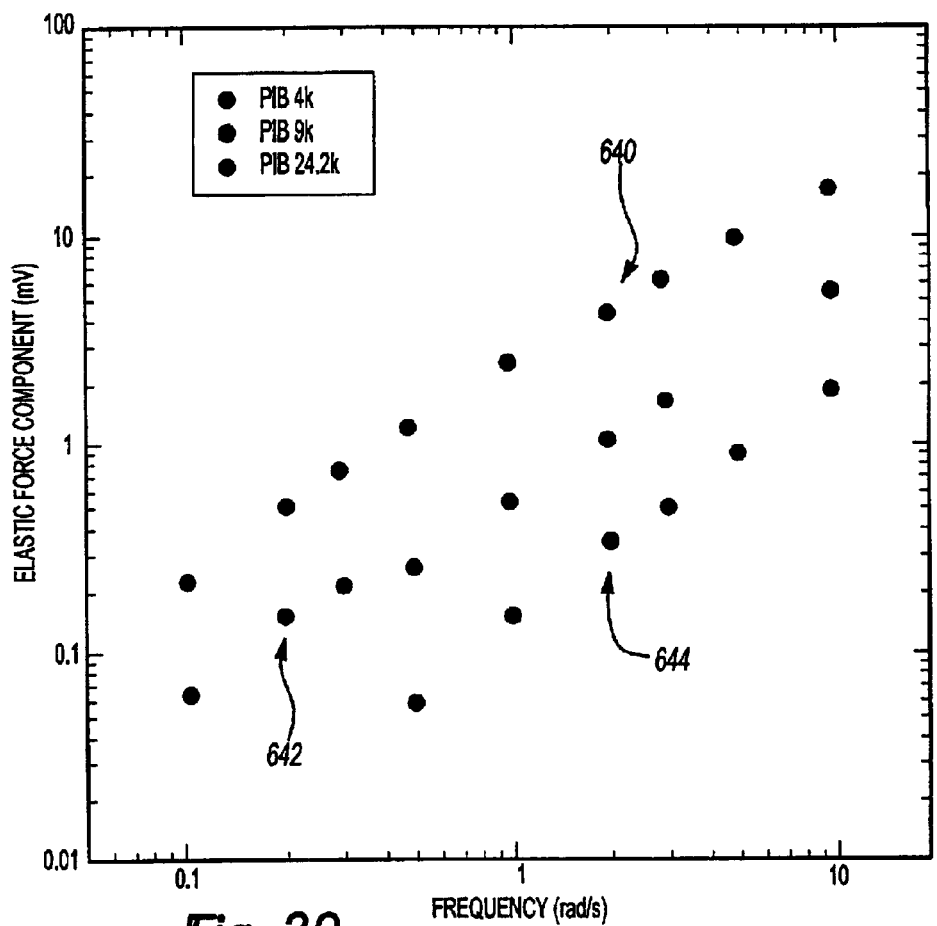
FIG. 20 shows $F'(\omega)$ for three polyisobutylene standards.

FIG. 19 and FIG. 20 show results from typical rheological measurements for various polyisobutylene (PIB) standards. FIG. 19 shows the real 620 and imaginary 622 parts, F'(ω) and F"(ω), of the force exerted on the test fixtures 542 by the fluid motion of one of the PIB samples ($9 \times 10^3$ weight average molecular weight). FIG. 20 shows F'(ω) for three 640, 642, 644 PIB standards, having weight average molecular weights of $24.2 \times 10^3$, $9 \times 10^3$, and $4 \times 10^3$, respectively.

Failure Characteristics

Failure of materials may be identified from a discontinuity in measured force-displacement curves. The stress and strain at failure may be calculated from this curve for specimens of known geometry; the toughness of the material, which is a measure of the energy involved in producing failure, may be estimated from the area under the stress-strain curve. If the sample is supported on a flexible substrate, though, these failure characteristics will reflect the properties of the sample-substrate composite.

One way to avoid such difficulties with flexural and tensile measurements involves using a material sample array 320 similar to the array shown in FIG. 8. However, when failure testing, the portions of the flexible substrate 324 within the circular perforations 334 are cut in half prior to deposition of the material samples 332. The samples 332 are deposited on the substrate 324 as described above, except care is taken to ensure that the material samples 332 extend across the cut edges of the substrate 324 without wetting the surface of the cut. Each of the resulting composites is deformed as described earlier for flexural or tensile measurements of Young's modulus: the sample array 320 is displaced away from the test fixtures 322 until failure occurs, as indicated by a discontinuity in the force-displacement curve. Although the resulting force-displacement curve may be used to determine Young's modulus, the deformation of uncut substrates is generally different than the deformation of cut substrates.

In an alternative approach, the material samples 332 are deposited on a thin, brittle substrate 324, such as a thin ceramic layer or rice paper, that will fail at small strains. Next, the PDMA 100 subjects the array 320 of composite films or membranes to flexural or tensile deformation, and the point at which the substrate 324 fails is identified by a discontinuity in the force-displacement curve. At the failure point, the mechanical load is completely transferred to the sample, and the test is continued until the sample fails.

Figure 21:
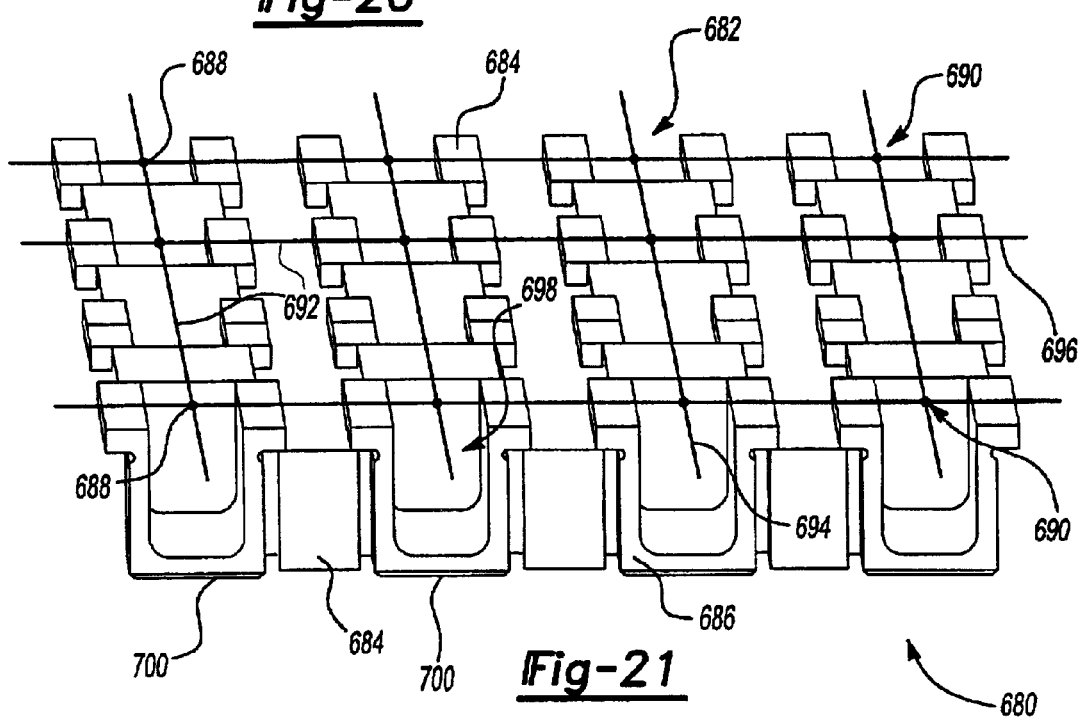
FIG. 21 shows a perspective view of test fixture for an embodiment for adhesive failure.

A third approach uses a sample holder 680 and sample array 682 shown in FIG. 21. The sample holder 680 comprises a frame 684 and U-shaped cups 686, and the sample array 682 includes material samples 688 deposited at intersections 690 of filamentous or rod-shaped substrates 692. Suitable substrate 692 materials include metals, ceramics, and fibers. The substrate 692 comprises lower 694 and upper 696 filaments, which are attached to the frame 684 and the U-shaped cups 686, respectively. The U-shaped cups 686 are slidably mounted in the frame 684 so that the lower 694 and upper 696 filaments intersect at right angles and at the center of the openings 698 of the U-shaped cups 686. When the bottoms 700 of the cups 686 are in contact with the probes 104, translating the sample holder 680 toward the probes 104 exerts a force on the cups 686, causing them to translate in a direction perpendicular to a plane containing the substrate 692. In the absence of material samples 688 at the substrate intersections 690, this motion causes the lower 694 and upper 696 filaments to separate.

To perform a failure test, the cups 686 are inserted in the frame 684 and the substrate 692 materials are laid up in the sample holder 680—first across the frame 684 and then across the cups 686. The lower 694 and upper 696 filaments are secured through mechanical clamping or gluing. If necessary, the filamentous substrates 692 are cut to permit independent motion of substrates 692 associated with different cups 686. One advantage of this latter design is that large numbers of filament intersections 690 (e.g. 96) may be assembled with limited numbers of substrate filaments 692 (e.g. 20). The material samples 688 are deposited at the substrate intersections 690 by liquid deposition and are annealed as necessary. The sample holder 680 is then attached to the second translation actuator 112.

Measurements may be performed in at least two ways. First, the sample array 682 and the probes 104 are translated relative to one another at a known velocity, beginning from a position in which none of the probes 104 are in contact with the cups 686 and ending with all of the cups 686 being displaced away from the frame 684 by a known amount. The latter position is generally selected to cause mechanical failure (separation) of the lower 694 and upper 696 filaments at all of the substrate intersections 690. The PDMA records the force exerted on each cup 686 at the sensors 106 either as a function of position, or as a function of time at a given position. In addition, the PDMA determines the maximum force at failure, the position where failure occurred, and the area under the force-displacement curve. If the sample dimensions are known, the stress and strain experienced by the material samples 688 may be calculated. Thus, PDMA may be used to measure stress-strain characteristics at large strains. Subsequent determination of the failure mechanism is generally done by visual inspection.

Second, the sample array 682 (sample holder 680) and the probes 106 are stepped through a series of relative displacements using the first (coarse) translation actuator 110. At each step, the second translation actuator 112 translates the sample array 682 in an oscillatory manner at a known amplitude and frequency and the stiffness of each material sample 688 is determined in the manner disclosed above for measuring modulus from flexure measurements at small strain. If the dimensions of the samples 688 are known, the stress and strain experienced by the material may be determined from the stiffness.

Adhesion—Probe Tack and Loop Tack

The PDMA can also be used to measure adhesion. The sample array generally comprises a substrate of known surface energy, and material samples that are deposited on predefined regions of the substrate's surface. Suitable substrates include metals (e.g. aluminum), polymeric films (e.g. polyimide or poly(ethylene terephthalate)), and semiconductors (e.g. polished silicon wafers). Suitable probe test fixtures have surfaces of known dimensions and surface energy and include an axially oriented stainless steel cylinder, a stainless steel hemisphere of known radius, and a loop formed from a strip of polymer film of known loop radius and width. The method generally comprises contacting each test fixture with a corresponding material sample for a fixed length of time; separating the test fixtures from the samples at a fixed velocity; and recording the forces required to separate the test fixtures from the samples.

Figure 22:
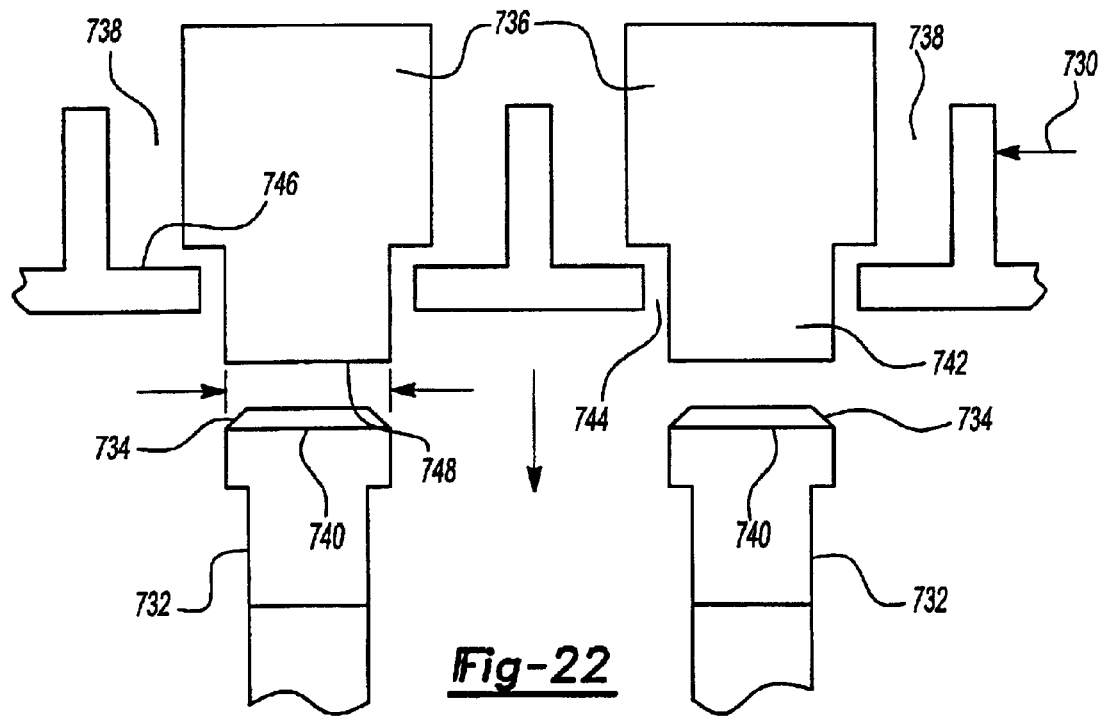
FIG. 22 shows a cross-sectional view of a first embodiment of a sample holder, a material sample array, and test fixtures that the PDMA of FIG. 1 can use to screen libraries of materials based on adhesion.

FIG. 22 shows a partial cross-sectional view of a first embodiment of a sample holder 730, test fixtures 732, and material samples 734, which the PDMA can use to screen libraries of materials based on tack. The sample holder 730 includes a group of weights 736, which initially rest in wells 738 formed in the sample holder 730. Each of the weights 736 is associated with one of the test fixtures 732, which has a working surface 740 of known composition and geometry, such as a stainless steel cylinder with a flat top. The weights 736 shown in FIG. 22 each have a relatively narrow base portion 742 that can pass through clearance holes 744 located in the bottom 746 of the wells 738. In addition, the clearance holes 744 are sized to admit the test fixtures 732 when the sample holder 730 is lowered onto the probes 104. The area of the working surface 740 of a particular test fixture 732 can be the same or different as the bottom surface 748 of a corresponding weight 736, though generally the areas are the same.

To perform a tack measurement, either the bottom surfaces 748 of the weights 736 or the working surfaces 740 of the test fixtures 732 are coated with the material samples 734 of known thicknesses (one sample 734 per test fixture 732). The PDMA then translates the sample holder 730 toward the probes 104, bringing the weights 736 and test fixtures 732 into contact. The PDMA then moves the sample holder 730 beyond the point of initial contact so that the weights 736 are supported by the test fixtures 732, which results in the application of a known force to the materials samples 734. After a set time has elapsed, the PDMA withdraws the sample holder 730 at a predetermined rate. During withdrawal, the bottoms of the wells 738 make contact with the weights 736, pulling each of the weights 736 from its corresponding test fixture 732. This force opposes a pre-load force applied to each of the sensors 106 by the flexure strips 150 (see discussion of FIG. 4). For a particular sensor 106, test fixture 732, and material sample 734, the resulting drop in the pre-load force relative to its steady state value is a measure of the adhesive force of the sample 734. Eventually the bond fails, and the sensor 106 reading returns to its steady state value. The area above the force sensor-displacement curve (measured with respect to the force applied by the weight) is a measure of the adhesion energy of the sample. The maximum elongation of the material sample 734 at failure can be estimated from the knowledge of the film thickness and the sample holder 730 position at failure.

Figure 23:
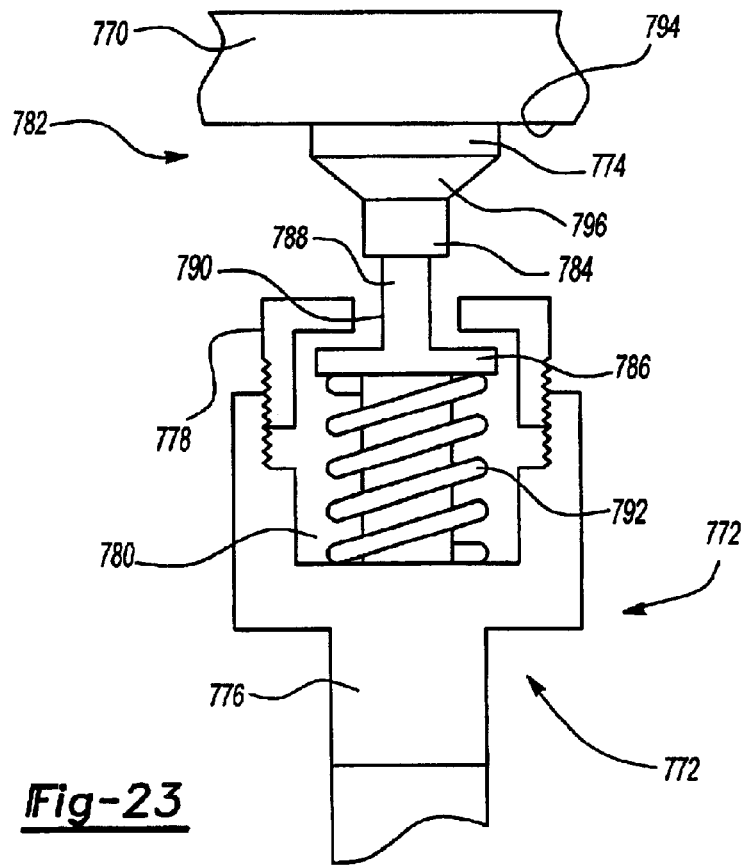
FIG. 23 shows a partial cross-sectional view of a second embodiment of a sample holder, a material sample array, and test fixtures that the PDMA of FIG. 1 can use to screen libraries of materials based on adhesion.

FIG. 23 shows a partial cross-sectional view of a second embodiment of a sample holder 770, test fixtures 772, and material samples 774, which can be used to screen libraries based on tack. Each of the test fixtures 772 comprises a hollow lower portion 776, which is connected to the base 192 of the probe 104, and a removable cap 778, which is threaded onto the lower portion 776 of the test fixture 772 forming a cavity 780. Each of the test fixtures 732 also includes a poppet 782 having head 784 and base 786 portions, and a relatively narrow neck 788 portion. The cap 778 has a clearance hole 790 that is sized to allow only the neck 788 portion to pass through, thereby allowing movement of the poppet 782 along the longitudinal axis of test fixture 772, while retaining the base 786 of the poppet 782 within the cavity 780. The test fixture 772 includes a compliant spring 792 located within the cavity 780, which exerts a force on the base 786 portion of the poppet 782. As can be seen in FIG. 23, the sample holder 770 has a generally flat surface 794 of known composition, such as stainless steel.

To perform a tack measurement, either the top surfaces 796 of the test fixtures 772 or the flat surface 794 of the sample holder 770 are coated with material samples 774 (one material sample 774 per test fixture 772). The PDMA then brings the flat surface 794 and the test fixtures 772 into contact so that the poppet 782 of each of the test fixtures 772 is compressed against the flat surface 794 of the sample holder 770. Because the spring 792 is more compliant than the sample holder 770 and other portions of the test fixtures 772, all of the poppets 782 experience nearly the same compressive force against the sample holder 770 despite any variations in heights of the test fixtures 772. After a set time has elapsed, the sample holder 770 is withdrawn at a predetermined rate. Although the poppets 782 initially remain attached to the flat surface 794 of the sample holder 770, the base 786 portion of the poppet 782 is retained in the cavity 780, resulting in a force that opposes the pre-load force applied to each of the sensors 106. This drop in the value of the pre-load force is measured by each of the sensors 106, and is analyzed in an identical manner to that given for the first embodiment shown in FIG. 22.

The PMDA using a sample holder 730 and test fixtures 732 shown in FIG. 22 was used to determine the adhesive characteristics of a commercially available formulation (BASF ACRONAL™ DS 3510 X). Approximately ten $\mu$l of this emulsion was deposited on the bottom surface 748 of a brass weight 736 and dried at room temperature and humidity for one hour to form a thin film of adhesive. The weight 736 was placed in the sample holder 730 of the PDMA with the bottom surface 748 facing the probes 104. The sample holder 730 was lowered at 25 $\mu$m/s so as to bring the weight 736 into contact with a stainless steel test fixtures 732 having a rounded tip with a ¹⁄₁₆ inch diameter. Upon contact, the sample holder 730 was held in position for 2000 $\mu$s before being retracted at a rate of 25 $\mu$m/s.

Figure 24:
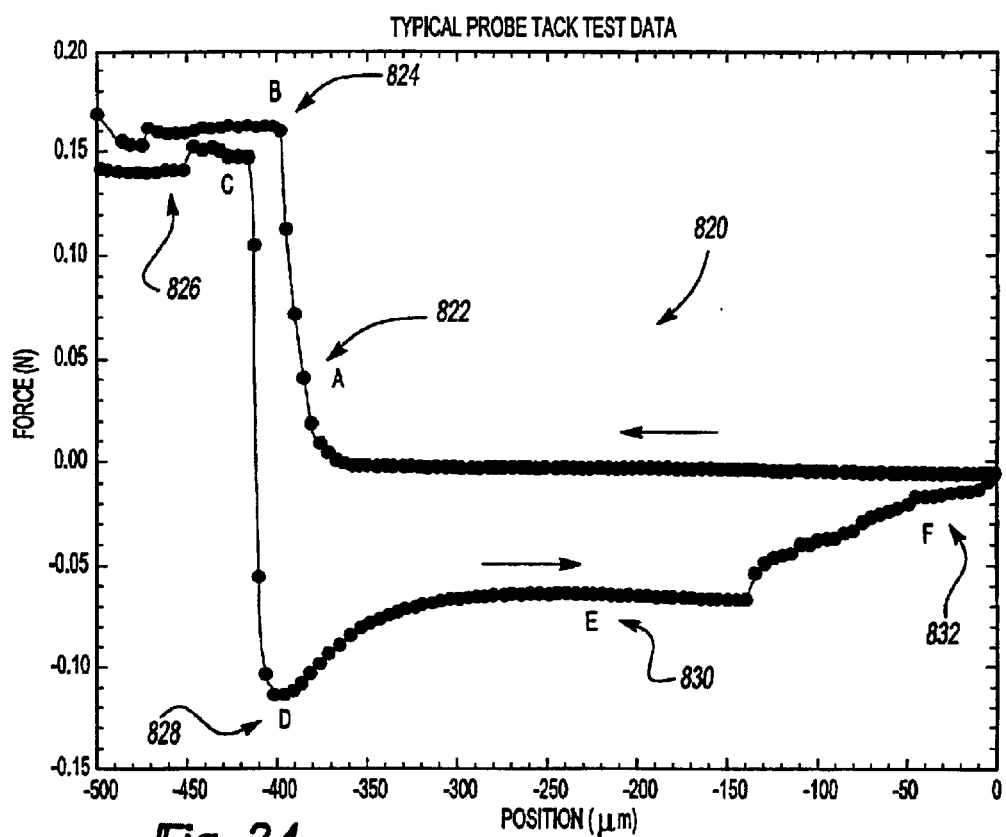
FIG. 24 shows a representative plot of force and sample holder displacement versus time for adhesion measurements using the sample holder, the material sample array and test fixtures shown in FIG. 22.

FIG. 24 shows a force-displacement curve 820 for this experiment. A first region 822 of the curve 820 exhibits a sharp increase in the force exerted on the test fixtures 732 once the weight 736 is brought into contact. The shape of this region 822 of the curve 820 reflects the penetration of the test fixture 732 through the adhesive layer on the bottom surface 748 of the weight 736. Within about 20 $\mu$m, the force reaches a relatively constant value of 0.16 N (second region 824) approximately equal to the weight of the probe 104. Upon retraction, the measured force remains high until the weight 736 is seated in the well 738 of the sample holder 730 (third region 826). The force then drops below the initial force measured when the weight 736 and the test fixture 732 are not in contact, reflecting the presence of a tensile force—an adhesive bond—between the weight 736 and the test fixture 732. (The offset value of the force resulting from pre-loading of the sensor 106 has been subtracted from these values; thus, tensile forces appear as negative values.) As shown by the fourth 828 and fifth 830 regions of the curve 820, this tensile force rises to a maximum value before falling off, possibly reflecting failure of the initial morphological structure within the adhesive and subsequent plastic deformation of the failed state. Eventually, the adhesive bond fails completely (sixth region 832), and the measured force approaches the value measured at the start of the experiment. An estimate of the work of adhesion may be made from the area between these two curves.

Example of Parallel Solid Modulus Measurements

The PDMA described herein was used to determine the solid modulus at small strains of a thin film of a commercial poly(styrene-block-butadiene-block-styrene) copolymer supplied by Aldrich. A sheet of polyimide (DuPont KAPTON HN™) 0.002" thick was mechanically clamped between the top and bottom sample plates and measured at an oscillation amplitude of 2.5 $\mu$m and a frequency of 10 Hz. The data were measured on two channels simultaneously and show a linear stiffness of 145 N/m; from the thickness of the polyimide and the dimensions of the clearance holes in the sample plates (0.250"), this corresponds to a solid modulus of 2300 MPa, in good agreement with previously published values for this material.

Figure 25:
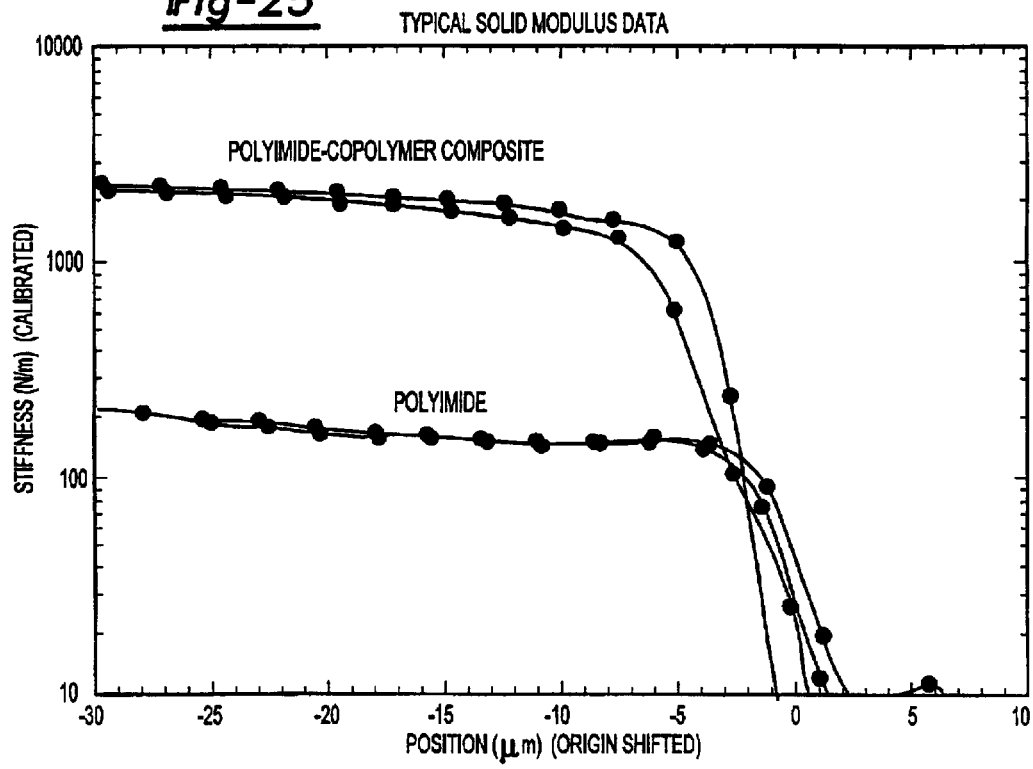
FIG. 25 is a graph of the results from the example.

A film of the block copolymer was prepared by casting from a 5 wt % solution in toluene onto a water surface at room temperature. Following the slow evaporation of the solvent, the film was dried for 2 hours in air and 12 hours in vacuum at room temperature before annealing for 12 hours under vacuum at 100° C. and 2 hours at 150° C. in order to remove all residual solvent and relax any mechanical stresses induced by the film casting procedure. A strip of material measuring 0.28×5.8×15.85 mm was cut from this film. The modulus of this strip was measured in a conventional dynamic mechanical thermal analyzer (Rheometrics DMTA-IV) to be 10±2 MPa over a frequency range from 1 to 1000 Hz. See FIG. 25. At the same time, a second strip of material 0.28 mm thick was glued to the previously measured piece of polyimide with a drop of toluene, permitted to dry for 2 hours in vacuum, and mechanically clamped between the top and bottom plates of the sample fixture. The stiffness of this composite material was measured on the same two channels simultaneously. From the linear stiffness of the composite (1340 N/m), the thicknesses of the polyimide and copolymer layers, and the previously measured modulus for polyimide, the modulus of the copolymer was measured to be 13.7 MPa, in good agreement with the value recorded by the conventional measurement.

It is to be understood that the above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A method of screening a combinatorial library of materials for at least one physical property, comprising:
   mechanically perturbing an array of a plurality of materials on a common substrate by applying a strain or a shear to at least two of the materials simultaneously with probes;
   monitoring, with a sensor, a force exerted by each of the materials in response to the mechanical perturbations, wherein the probe is located between the sensor and the material; and
   relating the monitored force to at least one physical property, wherein the physical property is selected from the group consisting of flexure, uniaxial extension, biaxial compression, shear, indentation, stress and strain at failure, tack, loop tack, Young's modulus, hardness, storage modulus, loss modulus and combinations thereof.

2. The method of claim 1, wherein the monitoring step comprises measuring, with the sensor, forces exerted on the probes by the materials as functions of displacement of a portion of the material or displacement of the probe.

3. The method of claim 1, wherein the monitoring step comprises measuring, with the sensor, forces exerted on the probes by the materials as functions of time.

4. The method of claim 1, wherein at least twelve materials are simultaneously mechanically perturbed.

5. The method of claim 1, wherein at least forty-eight materials are simultaneously mechanically perturbed.

6. The method of claim 1, wherein at least ninety-six materials are simultaneously mechanically perturbed.

7. The method of claim 1, wherein the probes comprise a test fixture.

8. A method of screening a combinatorial library of materials for at least one physical property, comprising:
   mechanically perturbing an array of a plurality of materials on a common substrate by contacting at least two of the materials simultaneously with probes;
   monitoring, with a sensor, a force exerted by each of the materials in response to the mechanical perturbations, wherein the sensor is responsive to tensile, compressive loads, or shear, and wherein the probe is located between the sensor and the material; and
   relating the monitored force to at least one physical property.

* * * * *

UNITED STATES PATENT AND TRADEMARK OFFICE
CERTIFICATE OF CORRECTION

PATENT NO. : 6,936,471 B2
DATED : August 30, 2005
INVENTOR(S) : Hajduk et al.

It is certified that error appears in the above-identified patent and that said Letters Patent is hereby corrected as shown below:

Title page,
Item [56], References Cited, U.S. PATENT DOCUMENTS,
"5,723,972 A        3/1998        Bartol et al." should be
-- 5,723,792 A      3/1998        Miyazaki --.

Signed and Sealed this

Seventh Day of February, 2006

JON W. DUDAS
*Director of the United States Patent and Trademark Office*